(12) United States Patent
Atanasoska et al.

(10) Patent No.: US 7,998,192 B2
(45) Date of Patent: Aug. 16, 2011

(54) ENDOPROSTHESES

(75) Inventors: Liliana Atanasoska, Edina, MN (US); Rajesh Radhakrishnan, Maple Grove, MN (US); Ben Arcand, Minneapolis, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 186 days.

(21) Appl. No.: 12/117,932

(22) Filed: May 9, 2008

(65) Prior Publication Data
US 2009/0281613 A1    Nov. 12, 2009

(51) Int. Cl.
A61F 2/06    (2006.01)
(52) U.S. Cl. .................................. 623/1.15; 623/1.46
(58) Field of Classification Search .............. 623/1.15, 623/1.34, 1.46, 1.38, 1.42
See application file for complete search history.

(56) References Cited

U.S. PATENT DOCUMENTS

| | | |
|---|---|---|
| 2,950,187 A | 8/1960 | Ototani |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |

(Continued)

FOREIGN PATENT DOCUMENTS
AU    739 507    11/1998
(Continued)

OTHER PUBLICATIONS
Cogger et al. "An Introduction to Electrochemical Impedance Measurement" 1999, 2-14.

(Continued)

*Primary Examiner* — Corrine M McDermott
*Assistant Examiner* — Rebecca Straszheim
(74) *Attorney, Agent, or Firm* — Fish & Richardson P.C.

(57) ABSTRACT

An endoprosthesis includes a body defining a flow passage therethrough. The body is capable of maintaining patency in a blood vessel and includes iron or an alloy thereof. The body has a nano-structured surface comprising iron oxide in which the individual nano-structures have a height to thickness aspect ratio of at least 5:1.

24 Claims, 5 Drawing Sheets

U.S. PATENT DOCUMENTS

| | | | |
|---|---|---|---|
| 4,784,659 A | 11/1988 | Fleckenstein et al. | |
| 4,800,882 A | 1/1989 | Gianturco | |
| 4,804,382 A | 2/1989 | Turina et al. | |
| 4,886,062 A | 12/1989 | Wiktor | |
| 4,954,126 A | 9/1990 | Wallsten | |
| 4,976,692 A | 12/1990 | Atad | |
| 4,994,071 A | 2/1991 | MacGregor | |
| 5,059,211 A | 10/1991 | Stack et al. | |
| 5,061,275 A | 10/1991 | Wallsten et al. | |
| 5,061,914 A | 10/1991 | Busch et al. | |
| 5,073,365 A | 12/1991 | Katz et al. | |
| 5,079,203 A | 1/1992 | Pinnavaia | |
| 5,091,024 A | 2/1992 | DeBold et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,234,457 A | 8/1993 | Andersen | |
| 5,236,413 A | 8/1993 | Feiring | |
| 5,236,447 A | 8/1993 | Kubo et al. | |
| 5,270,086 A | 12/1993 | Hamlin | |
| 5,279,292 A | 1/1994 | Baumann et al. | |
| 5,290,585 A | 3/1994 | Elton | |
| 5,292,558 A | 3/1994 | Heller et al. | |
| 5,302,414 A | 4/1994 | Alkhimov et al. | |
| 5,304,121 A | 4/1994 | Sahatjian | |
| 5,304,195 A | 4/1994 | Twyford, Jr. et al. | |
| 5,306,286 A | 4/1994 | Stack et al. | |
| 5,314,453 A | 5/1994 | Jeutter | |
| 5,322,520 A | 6/1994 | Milder | |
| 5,348,553 A | 9/1994 | Whitney | |
| 5,356,433 A | 10/1994 | Rowland et al. | |
| 5,360,440 A | 11/1994 | Andersen | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,385,776 A | 1/1995 | Maxfield et al. | |
| 5,397,307 A | 3/1995 | Goodin | |
| 5,405,367 A | 4/1995 | Schulman et al. | |
| 5,439,446 A | 8/1995 | Barry | |
| 5,443,458 A | 8/1995 | Eury | |
| 5,443,496 A | 8/1995 | Schwartz et al. | |
| 5,443,500 A | 8/1995 | Sigwart | |
| 5,449,373 A | 9/1995 | Pinchasik et al. | |
| 5,449,382 A | 9/1995 | Dayton | |
| 5,458,627 A | 10/1995 | Baranowski, Jr. et al. | |
| 5,462,575 A | 10/1995 | Del Corso | |
| 5,464,450 A | 11/1995 | Buscemi et al. | |
| 5,464,650 A | 11/1995 | Berg et al. | |
| 5,468,574 A | 11/1995 | Ehrenberg et al. | |
| 5,474,797 A | 12/1995 | Sioshansi et al. | |
| 5,500,013 A | 3/1996 | Buscemi et al. | |
| 5,527,337 A | 6/1996 | Stack et al. | |
| 5,536,573 A | 7/1996 | Rubner et al. | |
| 5,545,208 A | 8/1996 | Wolff et al. | |
| 5,549,664 A | 8/1996 | Hirata et al. | |
| 5,551,954 A | 9/1996 | Buscemi et al. | |
| 5,578,075 A | 11/1996 | Dayton | |
| 5,587,200 A | 12/1996 | Lorenz et al. | |
| 5,587,507 A | 12/1996 | Kohn et al. | |
| 5,591,222 A | 1/1997 | Susawa et al. | |
| 5,591,224 A | 1/1997 | Schwartz et al. | |
| 5,599,352 A | 2/1997 | Dinh et al. | |
| 5,603,556 A | 2/1997 | Klink | |
| 5,605,696 A | 2/1997 | Eury et al. | |
| 5,607,463 A | 3/1997 | Schwartz et al. | |
| 5,609,629 A | 3/1997 | Fearnot et al. | |
| 5,614,549 A | 3/1997 | Greenwald et al. | |
| 5,624,411 A | 4/1997 | Tuch | |
| 5,628,787 A | 5/1997 | Mayer | |
| 5,629,077 A | 5/1997 | Turnlund et al. | |
| 5,632,771 A | 5/1997 | Boatman et al. | |
| 5,632,840 A | 5/1997 | Campbell | |
| 5,649,951 A | 7/1997 | Davidson | |
| 5,658,327 A | 8/1997 | Altman et al. | |
| 5,672,242 A | 9/1997 | Jen | |
| 5,674,192 A | 10/1997 | Sahatjian et al. | |
| 5,674,242 A | 10/1997 | Phan et al. | |
| 5,676,685 A | 10/1997 | Razavi | |
| 5,679,440 A | 10/1997 | Kubota | |
| 5,690,670 A | 11/1997 | Davidson | |
| 5,693,085 A | 12/1997 | Buirge et al. | |
| 5,693,928 A | 12/1997 | Egitto et al. | |
| 5,697,967 A | 12/1997 | Dinh et al. | |
| 5,700,286 A | 12/1997 | Tartaglia et al. | |
| 5,716,981 A | 2/1998 | Hunter et al. | |
| 5,725,570 A | 3/1998 | Heath | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,749,880 A | 5/1998 | Banas et al. | |
| 5,758,562 A | 6/1998 | Thompson | |
| 5,761,775 A | 6/1998 | Legome et al. | |
| 5,769,883 A | 6/1998 | Buscemi et al. | |
| 5,773,925 A | 6/1998 | Kimura et al. | |
| 5,776,184 A | 7/1998 | Tuch | |
| 5,779,904 A | 7/1998 | Ruderman et al. | |
| 5,780,807 A | 7/1998 | Saunders | |
| 5,788,626 A | 8/1998 | Thompson | |
| 5,788,687 A | 8/1998 | Batich et al. | |
| 5,788,979 A | 8/1998 | Alt et al. | |
| 5,797,898 A | 8/1998 | Santini, Jr. et al. | |
| 5,800,511 A | 9/1998 | Mayer | |
| 5,815,904 A | 10/1998 | Clubb et al. | |
| 5,817,046 A | 10/1998 | Glickman | |
| 5,824,045 A | 10/1998 | Alt | |
| 5,824,048 A | 10/1998 | Tuch | |
| 5,824,077 A | 10/1998 | Mayer | |
| 5,830,217 A | 11/1998 | Ryan | |
| 5,833,715 A | 11/1998 | Vachon et al. | |
| 5,837,007 A | 11/1998 | Altman et al. | |
| 5,837,275 A | 11/1998 | Burrell et al. | |
| 5,840,387 A | 11/1998 | Berlowitz-Tarrant et al. | |
| 5,843,089 A | 12/1998 | Sahatjian et al. | |
| 5,843,172 A | 12/1998 | Yan | |
| 5,854,382 A | 12/1998 | Loomis | |
| 5,858,556 A | 1/1999 | Eckert et al. | |
| 5,869,140 A | 2/1999 | Blohowiak et al. | |
| 5,873,904 A | 2/1999 | Ragheb et al. | |
| 5,876,756 A | 3/1999 | Takada et al. | |
| 5,879,697 A | 3/1999 | Ding et al. | |
| 5,880,661 A | 3/1999 | Davidson et al. | |
| 5,882,335 A | 3/1999 | Leone et al. | |
| 5,891,108 A | 4/1999 | Leone et al. | |
| 5,891,191 A | 4/1999 | Stinson | |
| 5,899,935 A | 5/1999 | Ding | |
| 5,902,266 A | 5/1999 | Leone et al. | |
| 5,907,893 A | 6/1999 | Zadno-Azizi et al. | |
| 5,922,021 A | 7/1999 | Jang | |
| 5,928,247 A | 7/1999 | Barry et al. | |
| 5,935,506 A | 8/1999 | Schmitz et al. | |
| 5,938,903 A | 8/1999 | Broderick | |
| 5,941,843 A | 8/1999 | Atanasoska et al. | |
| 5,951,458 A | 9/1999 | Hastings et al. | |
| 5,951,881 A | 9/1999 | Rogers et al. | |
| 5,954,706 A | 9/1999 | Sahatjian | |
| 5,957,975 A | 9/1999 | Lafont et al. | |
| 5,958,440 A | 9/1999 | Burrell et al. | |
| 5,961,547 A | 10/1999 | Razavi | |
| 5,968,091 A | 10/1999 | Pinchuk et al. | |
| 5,968,092 A | 10/1999 | Buscemi et al. | |
| 5,972,027 A | 10/1999 | Johnson | |
| 5,972,192 A | 10/1999 | Dubin et al. | |
| 5,976,169 A | 11/1999 | Imran | |
| 5,976,454 A | 11/1999 | Sterzel et al. | |
| 5,977,204 A | 11/1999 | Boyan et al. | |
| 5,980,554 A | 11/1999 | Lenker et al. | |
| 5,980,564 A | 11/1999 | Stinson | |
| 5,980,566 A | 11/1999 | Alt et al. | |
| 6,001,125 A | 12/1999 | Golds et al. | |
| 6,013,591 A | 1/2000 | Ying et al. | |
| 6,017,553 A | 1/2000 | Burrell et al. | |

| | | | |
|---|---|---|---|
| 6,017,577 A | 1/2000 | Hostettler et al. | |
| 6,021,347 A | 2/2000 | Herbst et al. | |
| 6,025,036 A | 2/2000 | McGill et al. | |
| 6,027,742 A | 2/2000 | Lee et al. | |
| 6,034,295 A | 3/2000 | Rehberg et al. | |
| 6,063,101 A | 5/2000 | Jacobsen et al. | |
| 6,071,305 A | 6/2000 | Brown et al. | |
| 6,080,190 A | 6/2000 | Schwartz | |
| 6,086,773 A | 7/2000 | Dufresne et al. | |
| 6,096,070 A | 8/2000 | Ragheb et al. | |
| 6,096,175 A | 8/2000 | Roth | |
| 6,099,561 A | 8/2000 | Alt | |
| 6,099,562 A | 8/2000 | Ding et al. | |
| 6,106,473 A | 8/2000 | Violante et al. | |
| 6,107,004 A | 8/2000 | Donadio, III | |
| 6,117,592 A | 9/2000 | Hoshino et al. | |
| 6,120,535 A | 9/2000 | McDonald et al. | |
| 6,120,660 A | 9/2000 | Chu et al. | |
| 6,123,861 A | 9/2000 | Santini, Jr. et al. | |
| 6,132,463 A | 10/2000 | Lee et al. | |
| 6,139,573 A | 10/2000 | Sogard et al. | |
| 6,139,574 A | 10/2000 | Vacanti et al. | |
| 6,139,913 A | 10/2000 | Van Steenkiste et al. | |
| 6,140,740 A | 10/2000 | Porat et al. | |
| 6,143,370 A | 11/2000 | Panagiotou et al. | |
| 6,153,252 A | 11/2000 | Hossainy et al. | |
| 6,159,142 A | 12/2000 | Alt | |
| 6,162,238 A | 12/2000 | Kaplan et al. | |
| 6,164,284 A | 12/2000 | Schulman et al. | |
| 6,165,211 A | 12/2000 | Thompson | |
| 6,167,307 A | 12/2000 | Hess | |
| 6,168,602 B1 | 1/2001 | Ryan | |
| 6,174,329 B1 | 1/2001 | Callol et al. | |
| 6,174,330 B1 | 1/2001 | Stinson | |
| 6,180,222 B1 | 1/2001 | Schulz et al. | |
| 9,170,488 | 1/2001 | Spillman, Jr. et al. | |
| 6,185,455 B1 | 2/2001 | Loeb et al. | |
| 6,185,457 B1 | 2/2001 | Kroll et al. | |
| 6,190,404 B1 | 2/2001 | Palmaz et al. | |
| 6,192,271 B1 | 2/2001 | Hayman | |
| 6,201,991 B1 | 3/2001 | Chekanov | |
| 6,203,536 B1 | 3/2001 | Berg et al. | |
| 6,206,914 B1 | 3/2001 | Soykan et al. | |
| 6,206,915 B1 | 3/2001 | Fagan et al. | |
| 6,206,916 B1 | 3/2001 | Furst | |
| 6,212,434 B1 | 4/2001 | Scheiner | |
| 6,214,037 B1 | 4/2001 | Mitchell et al. | |
| 6,214,042 B1 | 4/2001 | Jacobsen et al. | |
| 6,217,607 B1 | 4/2001 | Alt | |
| 6,240,616 B1 | 6/2001 | Yan | |
| 6,241,762 B1 | 6/2001 | Shanley | |
| 6,245,103 B1 | 6/2001 | Stinson | |
| 6,245,104 B1 | 6/2001 | Alt | |
| 6,249,952 B1 | 6/2001 | Ding | |
| 6,251,136 B1 | 6/2001 | Guruwaiya et al. | |
| 6,251,980 B1 | 6/2001 | Lan et al. | |
| 6,253,252 B1 | 6/2001 | Schofield | |
| 6,253,443 B1 | 7/2001 | Johnson | |
| 6,254,632 B1 | 7/2001 | Wu et al. | |
| 6,258,117 B1 | 7/2001 | Camrud et al. | |
| 6,270,831 B2 | 8/2001 | Kumar et al. | |
| 6,273,908 B1 | 8/2001 | Ndondo-Lay | |
| 6,273,913 B1 | 8/2001 | Wright et al. | |
| 6,277,078 B1 | 8/2001 | Porat et al. | |
| 6,280,385 B1 | 8/2001 | Melzer et al. | |
| 6,280,411 B1 | 8/2001 | Lennox | |
| 6,283,386 B1 | 9/2001 | Van Steenkiste et al. | |
| 6,287,331 B1 | 9/2001 | Heath | |
| 6,287,332 B1 | 9/2001 | Bolz et al. | |
| 6,287,335 B1 | 9/2001 | Drasler et al. | |
| 6,287,628 B1 | 9/2001 | Hossainy et al. | |
| 6,290,721 B1 | 9/2001 | Heath | |
| 6,290,722 B1 | 9/2001 | Wang | |
| 6,291,076 B1 | 9/2001 | Nakatsugawa | |
| 6,299,604 B1 | 10/2001 | Ragheb et al. | |
| 6,299,755 B1 | 10/2001 | Richter | |
| 6,306,144 B1 | 10/2001 | Sydney et al. | |
| 6,309,414 B1 | 10/2001 | Rolando et al. | |
| 6,312,463 B1 | 11/2001 | Rourke et al. | |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,419,692 B1 | 7/2002 | Yang et al. |
| 6,423,092 B2 | 7/2002 | Datta et al. |
| 6,436,133 B1 | 8/2002 | Furst et al. |
| 6,440,166 B1 | 8/2002 | Kolluri |
| 6,440,487 B1 | 8/2002 | Delfino et al. |
| 6,447,540 B1 | 9/2002 | Fontaine et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,492,096 B1 | 12/2002 | Liu et al. |
| 6,503,556 B1 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Wu et al. |

| | | |
|---|---|---|
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Langford et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,077,859 B2 | 7/2006 | Sirhan et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 * | 9/2006 | Hamm et al. ............... 623/1.42 |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 * | 1/2007 | Kramer ........................ 427/189 |
| 7,169,178 B1 | 1/2007 | Santos et al. |
| 7,195,640 B2 | 3/2007 | Falotico et al. |

| | | | | | |
|---|---|---|---|---|---|
| 7,195,641 B2 | 3/2007 | Palmaz et al. | 2002/0103528 A1 | 8/2002 | Schaldach et al. |
| 7,198,675 B2 | 4/2007 | Fox et al. | 2002/0111694 A1 | 8/2002 | Ellingsen et al. |
| 7,208,011 B2 * | 4/2007 | Shanley et al. ............... 623/1.42 | 2002/0121497 A1 | 9/2002 | Tomonto |
| 7,208,172 B2 | 4/2007 | Birdsall et al. | 2002/0123801 A1 | 9/2002 | Pacetti et al. |
| 7,220,816 B2 | 5/2007 | Pacetti | 2002/0133222 A1 | 9/2002 | Das |
| 7,229,471 B2 | 6/2007 | Gale et al. | 2002/0133224 A1 | 9/2002 | Bajgar et al. |
| 7,235,096 B1 | 6/2007 | Van Tassel et al. | 2002/0138100 A1 | 9/2002 | Stoll et al. |
| 7,235,098 B2 | 6/2007 | Palmaz | 2002/0138131 A1 | 9/2002 | Solovay et al. |
| 7,238,199 B2 | 7/2007 | Feldman et al. | 2002/0138136 A1 | 9/2002 | Chandresekaran et al. |
| 7,241,295 B2 | 7/2007 | Maguire | 2002/0138154 A1 | 9/2002 | Li et al. |
| 7,244,272 B2 | 7/2007 | Dubson et al. | 2002/0144757 A1 | 10/2002 | Craig et al. |
| 7,261,732 B2 | 8/2007 | Justino | 2002/0155212 A1 | 10/2002 | Hossainy |
| 7,261,735 B2 | 8/2007 | Llanos et al. | 2002/0165265 A1 | 11/2002 | Hunter et al. |
| 7,267,960 B2 | 9/2007 | Galibert et al. | 2002/0165578 A1 | 11/2002 | Sawitowski et al. |
| 7,279,174 B2 | 10/2007 | Pacetti | 2002/0165600 A1 | 11/2002 | Banas et al. |
| 7,279,175 B2 | 10/2007 | Chen et al. | 2002/0165607 A1 | 11/2002 | Alt |
| 7,294,409 B2 | 11/2007 | Lye et al. | 2002/0169493 A1 | 11/2002 | Widenhouse et al. |
| 7,311,727 B2 | 12/2007 | Mazumder et al. | 2002/0178570 A1 | 12/2002 | Sogard et al. |
| 7,323,189 B2 | 1/2008 | Pathak | 2002/0182241 A1 | 12/2002 | Borenstein et al. |
| 7,331,993 B2 | 2/2008 | White | 2002/0183581 A1 | 12/2002 | Yoe et al. |
| 7,335,375 B2 | 2/2008 | Li et al. | 2002/0183682 A1 | 12/2002 | Darvish et al. |
| 7,344,560 B2 | 3/2008 | Gregorich et al. | 2002/0187260 A1 | 12/2002 | Sheppard, Jr. et al. |
| 7,344,563 B2 | 3/2008 | Vallana et al. | 2002/0193336 A1 | 12/2002 | Elkins et al. |
| 7,393,589 B2 | 7/2008 | Aharonov et al. | 2002/0193869 A1 | 12/2002 | Dang |
| 7,402,173 B2 | 7/2008 | Scheuermann et al. | 2002/0197178 A1 | 12/2002 | Yan |
| 7,416,558 B2 | 8/2008 | Yip et al. | 2002/0198601 A1 | 12/2002 | Bales et al. |
| 7,432,327 B2 | 10/2008 | Glasgow et al. | 2003/0003127 A1 | 1/2003 | Brown et al. |
| 7,462,366 B2 | 12/2008 | Lanphere | 2003/0003220 A1 | 1/2003 | Zhong et al. |
| 7,498,385 B2 | 3/2009 | Swetlin et al. | 2003/0004563 A1 | 1/2003 | Jackson et al. |
| 7,507,433 B2 | 3/2009 | Weber | 2003/0004564 A1 | 1/2003 | Elkins et al. |
| 7,537,610 B2 | 5/2009 | Reiss | 2003/0009214 A1 | 1/2003 | Shanley |
| 7,547,445 B2 | 6/2009 | Chudzik et al. | 2003/0018380 A1 | 1/2003 | Craig et al. |
| 7,563,277 B2 * | 7/2009 | Case et al. ................... 623/1.36 | 2003/0018381 A1 | 1/2003 | Whitcher et al. |
| 7,637,941 B1 | 12/2009 | Manicka et al. | 2003/0023300 A1 | 1/2003 | Bailey et al. |
| 7,651,527 B2 | 1/2010 | Krivoruchko et al. | 2003/0028242 A1 | 2/2003 | Vallana et al. |
| 7,691,401 B2 | 4/2010 | Castro et al. | 2003/0028243 A1 | 2/2003 | Bates et al. |
| 7,713,297 B2 | 5/2010 | Alt | 2003/0032892 A1 | 2/2003 | Erlach et al. |
| 7,749,264 B2 | 7/2010 | Gregorich et al. | 2003/0033007 A1 | 2/2003 | Sirhan et al. |
| 7,758,635 B2 | 7/2010 | Parsonage | 2003/0044446 A1 | 3/2003 | Moro et al. |
| 7,771,773 B2 | 8/2010 | Namavar | 2003/0050687 A1 | 3/2003 | Schwade et al. |
| 7,776,926 B1 | 8/2010 | Claude et al. | 2003/0059640 A1 | 3/2003 | Marton et al. |
| 2001/0001834 A1 | 5/2001 | Palmaz et al. | 2003/0060871 A1 | 3/2003 | Hill et al. |
| 2001/0002000 A1 | 5/2001 | Kumar et al. | 2003/0060873 A1 | 3/2003 | Gertner et al. |
| 2001/0002435 A1 | 5/2001 | Berg et al. | 2003/0064095 A1 | 4/2003 | Martin et al. |
| 2001/0013166 A1 | 8/2001 | Yan | 2003/0068355 A1 | 4/2003 | Shanley et al. |
| 2001/0021871 A1 | 9/2001 | Stinson | 2003/0074053 A1 | 4/2003 | Palmaz et al. |
| 2001/0021873 A1 | 9/2001 | Stinson | 2003/0077200 A1 | 4/2003 | Craig et al. |
| 2001/0027299 A1 | 10/2001 | Yang et al. | 2003/0077310 A1 | 4/2003 | Pathak et al. |
| 2001/0029398 A1 | 10/2001 | Jadhav | 2003/0083614 A1 | 5/2003 | Eisert |
| 2001/0029660 A1 | 10/2001 | Johnson | 2003/0083646 A1 | 5/2003 | Sirhan et al. |
| 2001/0032011 A1 | 10/2001 | Stanford | 2003/0083731 A1 | 5/2003 | Kramer et al. |
| 2001/0032013 A1 | 10/2001 | Marton | 2003/0087024 A1 | 5/2003 | Flanagan |
| 2001/0032014 A1 | 10/2001 | Yang et al. | 2003/0088307 A1 | 5/2003 | Shulze et al. |
| 2001/0044650 A1 | 11/2001 | Simso et al. | 2003/0088312 A1 | 5/2003 | Kopia et al. |
| 2002/0000175 A1 | 1/2002 | Hintermaier et al. | 2003/0099684 A1 | 5/2003 | Domb |
| 2002/0000406 A1 | 1/2002 | Izumi | 2003/0100815 A1 | 5/2003 | Da Silva et al. |
| 2002/0004060 A1 | 1/2002 | Heublein et al. | 2003/0100830 A1 | 5/2003 | Zhong et al. |
| 2002/0007102 A1 | 1/2002 | Salmon et al. | 2003/0104030 A1 | 6/2003 | Igaki et al. |
| 2002/0007209 A1 | 1/2002 | Scheerder et al. | 2003/0105511 A1 | 6/2003 | Welsh et al. |
| 2002/0010505 A1 | 1/2002 | Richter | 2003/0108659 A1 | 6/2003 | Bales et al. |
| 2002/0016623 A1 | 2/2002 | Kula et al. | 2003/0114917 A1 | 6/2003 | Holloway et al. |
| 2002/0016624 A1 | 2/2002 | Patterson et al. | 2003/0114921 A1 | 6/2003 | Yoon |
| 2002/0028827 A1 | 3/2002 | Naicker et al. | 2003/0118692 A1 | 6/2003 | Wang et al. |
| 2002/0032477 A1 | 3/2002 | Helmus et al. | 2003/0120339 A1 | 6/2003 | Banik et al. |
| 2002/0035394 A1 | 3/2002 | Fierens et al. | 2003/0124055 A1 | 7/2003 | Li et al. |
| 2002/0038146 A1 | 3/2002 | Harry | 2003/0125803 A1 | 7/2003 | Vallana |
| 2002/0042039 A1 | 4/2002 | Kim et al. | 2003/0130718 A1 | 7/2003 | Palmas et al. |
| 2002/0049495 A1 | 4/2002 | Kutryk et al. | 2003/0139799 A1 | 7/2003 | Ley et al. |
| 2002/0051730 A1 | 5/2002 | Bodnar et al. | 2003/0143330 A1 | 7/2003 | Loomis et al. |
| 2002/0051846 A1 | 5/2002 | Kirkpatrick et al. | 2003/0144728 A1 | 7/2003 | Scheuermann et al. |
| 2002/0065553 A1 | 5/2002 | Weber | 2003/0150380 A1 | 8/2003 | Yoe |
| 2002/0082679 A1 | 6/2002 | Sirhan et al. | 2003/0153901 A1 | 8/2003 | Herweck et al. |
| 2002/0087123 A1 | 7/2002 | Hossainy et al. | 2003/0158598 A1 | 8/2003 | Ashton et al. |
| 2002/0090313 A1 | 7/2002 | Wang et al. | 2003/0170605 A1 | 9/2003 | Long et al. |
| 2002/0091375 A1 | 7/2002 | Sahatjian et al. | 2003/0181975 A1 | 9/2003 | Ishii et al. |
| 2002/0098278 A1 | 7/2002 | Bates et al. | 2003/0185895 A1 | 10/2003 | Lanphere |
| 2002/0099434 A1 | 7/2002 | Buscemi et al. | 2003/0190406 A1 | 10/2003 | Hossainy et al. |
| 2002/0099438 A1 | 7/2002 | Furst | 2003/0195613 A1 | 10/2003 | Curcio et al. |
| 2002/0103527 A1 | 8/2002 | Kocur et al. | 2003/0204239 A1 | 10/2003 | Carlyle et al. |

| | | | | | | |
|---|---|---|---|---|---|---|
| 2003/0211135 A1 | 11/2003 | Greenhalgh et al. | 2004/0220662 A1 | 11/2004 | Dang et al. | |
| 2003/0216803 A1 | 11/2003 | Ledergerber | 2004/0224001 A1 | 11/2004 | Pacetti et al. | |
| 2003/0219562 A1 | 11/2003 | Rypacek et al. | 2004/0225346 A1 | 11/2004 | Mazumder et al. | |
| 2003/0221307 A1 | 12/2003 | Kaese et al. | 2004/0228905 A1 | 11/2004 | Greenspan et al. | |
| 2003/0228523 A1 | 12/2003 | DeLongchamp et al. | 2004/0230176 A1 | 11/2004 | Shanahan et al. | |
| 2003/0236513 A1 | 12/2003 | Schwarz et al. | 2004/0230225 A1 | 11/2004 | Penner et al. | |
| 2004/0000046 A1 | 1/2004 | Stinson | 2004/0230290 A1 | 11/2004 | Weber et al. | |
| 2004/0000540 A1 | 1/2004 | Soboyejo et al. | 2004/0230293 A1 | 11/2004 | Yip et al. | |
| 2004/0006382 A1 | 1/2004 | Sohier | 2004/0234737 A1 | 11/2004 | Pacetti | |
| 2004/0018296 A1 | 1/2004 | Castro et al. | 2004/0236415 A1 | 11/2004 | Thomas | |
| 2004/0019376 A1 | 1/2004 | Alt | 2004/0236416 A1 | 11/2004 | Falotico | |
| 2004/0022939 A1 | 2/2004 | Kim et al. | 2004/0237282 A1 | 12/2004 | Hines | |
| 2004/0024448 A1 | 2/2004 | Chang et al. | 2004/0242106 A1 | 12/2004 | Rabasco et al. | |
| 2004/0029303 A1 | 2/2004 | Hart et al. | 2004/0243217 A1 | 12/2004 | Andersen | |
| 2004/0030218 A1 | 2/2004 | Kocur et al. | 2004/0243237 A1 | 12/2004 | Unwin et al. | |
| 2004/0034409 A1 | 2/2004 | Heublein et al. | 2004/0243241 A1 | 12/2004 | Istephanous et al. | |
| 2004/0039438 A1 | 2/2004 | Alt | 2004/0247671 A1 | 12/2004 | Prescott et al. | |
| 2004/0039441 A1 | 2/2004 | Rowland et al. | 2004/0249440 A1 | 12/2004 | Bucker et al. | |
| 2004/0044397 A1 | 3/2004 | Stinson | 2004/0249443 A1 | 12/2004 | Shanley et al. | |
| 2004/0047980 A1 | 3/2004 | Pacetti et al. | 2004/0249444 A1 | 12/2004 | Reiss | |
| 2004/0059407 A1 | 3/2004 | Escamilla et al. | 2004/0249445 A1 | 12/2004 | Rosenthal et al. | |
| 2004/0059409 A1 | 3/2004 | Stenzel | 2004/0249449 A1 | 12/2004 | Shanley et al. | |
| 2004/0067301 A1 | 4/2004 | Ding | 2004/0254419 A1* | 12/2004 | Wang et al. | 600/8 |
| 2004/0071861 A1 | 4/2004 | Mandrusov et al. | 2004/0254635 A1 | 12/2004 | Shanley et al. | |
| 2004/0073155 A1 | 4/2004 | Laufer et al. | 2005/0004661 A1 | 1/2005 | Lewis et al. | |
| 2004/0073284 A1 | 4/2004 | Bates et al. | 2005/0010275 A1 | 1/2005 | Sahatjian | |
| 2004/0073293 A1 | 4/2004 | Thompson | 2005/0010279 A1 | 1/2005 | Tenerz et al. | |
| 2004/0073297 A1 | 4/2004 | Rohde et al. | 2005/0015142 A1 | 1/2005 | Austin et al. | |
| 2004/0073298 A1 | 4/2004 | Hossainy | 2005/0019265 A1 | 1/2005 | Hammer et al. | |
| 2004/0078071 A1 | 4/2004 | Escamilla et al. | 2005/0019371 A1 | 1/2005 | Anderson et al. | |
| 2004/0082682 A1 | 4/2004 | Loomis et al. | 2005/0021127 A1 | 1/2005 | Kawula | |
| 2004/0088038 A1 | 5/2004 | Dehnad et al. | 2005/0021128 A1 | 1/2005 | Nakahama et al. | |
| 2004/0088041 A1 | 5/2004 | Stanford | 2005/0022627 A1 | 2/2005 | Chen | |
| 2004/0093071 A1 | 5/2004 | Jang | 2005/0027350 A1 | 2/2005 | Momma et al. | |
| 2004/0093075 A1 | 5/2004 | Kuehne | 2005/0033407 A1 | 2/2005 | Weber et al. | |
| 2004/0093076 A1 | 5/2004 | White et al. | 2005/0033411 A1 | 2/2005 | Wu et al. | |
| 2004/0098089 A1 | 5/2004 | Weber | 2005/0033412 A1 | 2/2005 | Wu et al. | |
| 2004/0098108 A1 | 5/2004 | Harder et al. | 2005/0033417 A1 | 2/2005 | Borges et al. | |
| 2004/0098119 A1 | 5/2004 | Wang | 2005/0037047 A1 | 2/2005 | Song | |
| 2004/0106975 A1 | 6/2004 | Solovay et al. | 2005/0037050 A1 | 2/2005 | Weber | |
| 2004/0106984 A1 | 6/2004 | Stinson | 2005/0038134 A1 | 2/2005 | Loomis et al. | |
| 2004/0106985 A1 | 6/2004 | Jang | 2005/0038501 A1 | 2/2005 | Moore, Jr. et al. | |
| 2004/0111150 A1 | 6/2004 | Berg et al. | 2005/0042288 A1 | 2/2005 | Koblish et al. | |
| 2004/0116999 A1 | 6/2004 | Ledergerber | 2005/0042440 A1 | 2/2005 | Bach et al. | |
| 2004/0117005 A1 | 6/2004 | Gadde et al. | 2005/0055044 A1 | 3/2005 | Kangas | |
| 2004/0117008 A1 | 6/2004 | Wnendt et al. | 2005/0055080 A1 | 3/2005 | Istephanous et al. | |
| 2004/0122504 A1 | 6/2004 | Hogendijk | 2005/0055085 A1 | 3/2005 | Rivron et al. | |
| 2004/0126566 A1 | 7/2004 | Axen et al. | 2005/0060020 A1 | 3/2005 | Jenson | |
| 2004/0133270 A1 | 7/2004 | Grandt | 2005/0060021 A1 | 3/2005 | O'Brien et al. | |
| 2004/0134886 A1 | 7/2004 | Wagner et al. | 2005/0064088 A1 | 3/2005 | Fredrickson | |
| 2004/0137039 A1 | 7/2004 | Sukhishvili et al. | 2005/0069630 A1 | 3/2005 | Fox et al. | |
| 2004/0138738 A1 | 7/2004 | Stinson | 2005/0070989 A1 | 3/2005 | Lye et al. | |
| 2004/0142014 A1 | 7/2004 | Litvack et al. | 2005/0070990 A1 | 3/2005 | Stinson | |
| 2004/0143317 A1 | 7/2004 | Stinson et al. | 2005/0070996 A1 | 3/2005 | Dinh et al. | |
| 2004/0143321 A1 | 7/2004 | Litvack et al. | 2005/0071016 A1 | 3/2005 | Hausdorf et al. | |
| 2004/0148010 A1 | 7/2004 | Rush | 2005/0072544 A1 | 4/2005 | Palmaz et al. | |
| 2004/0148015 A1 | 7/2004 | Lye et al. | 2005/0074479 A1 | 4/2005 | Weber et al. | |
| 2004/0153138 A1 | 8/2004 | Murphy | 2005/0074545 A1 | 4/2005 | Thomas | |
| 2004/0157073 A1 | 8/2004 | Burrell et al. | 2005/0077305 A1 | 4/2005 | Guevara | |
| 2004/0158308 A1 | 8/2004 | Hogendijk et al. | 2005/0079132 A1 | 4/2005 | Wang et al. | |
| 2004/0158310 A1 | 8/2004 | Weber et al. | 2005/0079199 A1 | 4/2005 | Heruth et al. | |
| 2004/0167572 A1 | 8/2004 | Roth et al. | 2005/0079356 A1 | 4/2005 | Rathenow et al. | |
| 2004/0167612 A1 | 8/2004 | Grignani et al. | 2005/0092615 A1 | 5/2005 | Birdsall et al. | |
| 2004/0172124 A1 | 9/2004 | Vallana et al. | 2005/0096731 A1 | 5/2005 | Looi et al. | |
| 2004/0181252 A1 | 9/2004 | Boyle et al. | 2005/0100577 A1 | 5/2005 | Parker et al. | |
| 2004/0181275 A1 | 9/2004 | Noble et al. | 2005/0100609 A1 | 5/2005 | Claude | |
| 2004/0181276 A1 | 9/2004 | Brown et al. | 2005/0102025 A1 | 5/2005 | Laroche et al. | |
| 2004/0181278 A1 | 9/2004 | Tseng et al. | 2005/0106212 A1 | 5/2005 | Gertner et al. | |
| 2004/0182511 A1 | 9/2004 | Rakos et al. | 2005/0107869 A1 | 5/2005 | Sirhan et al. | |
| 2004/0186553 A1 | 9/2004 | Yan | 2005/0107870 A1 | 5/2005 | Wang et al. | |
| 2004/0191293 A1 | 9/2004 | Claude | 2005/0113936 A1 | 5/2005 | Brustad et al. | |
| 2004/0191404 A1 | 9/2004 | Hossainy et al. | 2005/0119723 A1 | 6/2005 | Peacock | |
| 2004/0202692 A1 | 10/2004 | Shanley et al. | 2005/0129727 A1 | 6/2005 | Weber et al. | |
| 2004/0204750 A1 | 10/2004 | Dinh | 2005/0131509 A1 | 6/2005 | Atanassoska et al. | |
| 2004/0211362 A1 | 10/2004 | Castro et al. | 2005/0131521 A1 | 6/2005 | Marton | |
| 2004/0219214 A1 | 11/2004 | Gravett et al. | 2005/0131522 A1 | 6/2005 | Stinson et al. | |
| 2004/0220510 A1 | 11/2004 | Koullick et al. | 2005/0131527 A1 | 6/2005 | Pathak | |
| 2004/0220659 A1 | 11/2004 | Girton | 2005/0131528 A1 | 6/2005 | Buscemi et al. | |
| 2004/0220660 A1 | 11/2004 | Shanley et al. | 2005/0136090 A1 | 6/2005 | Falotico et al. | |

| | | | | | |
|---|---|---|---|---|---|
| 2005/0137677 A1 | 6/2005 | Rush | 2006/0052744 A1 | 3/2006 | Weber |
| 2005/0137679 A1 | 6/2005 | Changelian et al. | 2006/0052863 A1 | 3/2006 | Harder et al. |
| 2005/0137684 A1 | 6/2005 | Changelian et al. | 2006/0052864 A1 | 3/2006 | Harder et al. |
| 2005/0149169 A1 | 7/2005 | Wang et al. | 2006/0058868 A1 | 3/2006 | Gale et al. |
| 2005/0149170 A1 | 7/2005 | Tassel et al. | 2006/0062820 A1 | 3/2006 | Gertner et al. |
| 2005/0149175 A1 | 7/2005 | Hunter et al. | 2006/0064160 A1 | 3/2006 | Gerold et al. |
| 2005/0149177 A1 | 7/2005 | Weber et al. | 2006/0067908 A1 | 3/2006 | Ding |
| 2005/0159804 A1 | 7/2005 | Lad et al. | 2006/0069427 A1 | 3/2006 | Savage et al. |
| 2005/0159805 A1 | 7/2005 | Weber et al. | 2006/0075044 A1 | 4/2006 | Fox et al. |
| 2005/0159809 A1 | 7/2005 | Hezi-Yamit et al. | 2006/0075092 A1 | 4/2006 | Kidokoro |
| 2005/0160600 A1 | 7/2005 | Bien et al. | 2006/0085062 A1 | 4/2006 | Lee et al. |
| 2005/0163821 A1 | 7/2005 | Sung et al. | 2006/0085065 A1 | 4/2006 | Krause et al. |
| 2005/0163954 A1 | 7/2005 | Shaw | 2006/0088566 A1 | 4/2006 | Parsonage et al. |
| 2005/0165301 A1 | 7/2005 | Smith et al. | 2006/0088567 A1 | 4/2006 | Warner et al. |
| 2005/0165468 A1 | 7/2005 | Marton | 2006/0088653 A1 | 4/2006 | Chappa et al. |
| 2005/0165470 A1 | 7/2005 | Weber | 2006/0088666 A1 | 4/2006 | Kobrin et al. |
| 2005/0169969 A1 | 8/2005 | Li et al. | 2006/0100696 A1 | 5/2006 | Atanasoska et al. |
| 2005/0171595 A1 | 8/2005 | Feldman et al. | 2006/0115512 A1 | 6/2006 | Peacock et al. |
| 2005/0177226 A1 | 8/2005 | Banik et al. | 2006/0118236 A1 | 6/2006 | House et al. |
| 2005/0180919 A1 | 8/2005 | Tedeschi | 2006/0121080 A1 | 6/2006 | Lye et al. |
| 2005/0182361 A1 | 8/2005 | Lennox | 2006/0122694 A1 | 6/2006 | Stinson et al. |
| 2005/0182478 A1 | 8/2005 | Holman et al. | 2006/0122697 A1 | 6/2006 | Shanley et al. |
| 2005/0186250 A1 | 8/2005 | Gertner et al. | 2006/0124472 A1 | 6/2006 | Rokicki |
| 2005/0187611 A1 | 8/2005 | Ding et al. | 2006/0127266 A1 | 6/2006 | Miura et al. |
| 2005/0192657 A1 | 9/2005 | Colen et al. | 2006/0129215 A1 | 6/2006 | Helmus et al. |
| 2005/0192662 A1 | 9/2005 | Ward | 2006/0129222 A1 | 6/2006 | Stinson |
| 2005/0192664 A1 | 9/2005 | Eisert | 2006/0129225 A1 | 6/2006 | Kopia et al. |
| 2005/0196424 A1 | 9/2005 | Chappa | 2006/0136048 A1 | 6/2006 | Pacetti et al. |
| 2005/0208098 A1 | 9/2005 | Castro et al. | 2006/0141156 A1 | 6/2006 | Viel et al. |
| 2005/0208100 A1 | 9/2005 | Weber et al. | 2006/0149352 A1 | 7/2006 | Schlun |
| 2005/0209680 A1 | 9/2005 | Gale et al. | 2006/0153729 A1 | 7/2006 | Stinson et al. |
| 2005/0209681 A1 | 9/2005 | Curcio et al. | 2006/0155361 A1 | 7/2006 | Schomig et al. |
| 2005/0211680 A1 | 9/2005 | Li et al. | 2006/0167543 A1 | 7/2006 | Bailey et al. |
| 2005/0214951 A1 | 9/2005 | Nahm et al. | 2006/0177480 A1 | 8/2006 | Sung et al. |
| 2005/0216074 A1 | 9/2005 | Sahatjian | 2006/0178727 A1 | 8/2006 | Richter |
| 2005/0216075 A1 | 9/2005 | Wang et al. | 2006/0184235 A1 | 8/2006 | Rivron et al. |
| 2005/0220853 A1 | 10/2005 | Dao et al. | 2006/0193886 A1 | 8/2006 | Owens et al. |
| 2005/0221072 A1 * | 10/2005 | Dubrow et al. ............ 428/292.1 | 2006/0193887 A1 | 8/2006 | Owens et al. |
| 2005/0222671 A1 | 10/2005 | Schaeffer et al. | 2006/0193888 A1 | 8/2006 | Lye et al. |
| 2005/0228477 A1 | 10/2005 | Grainger et al. | 2006/0193889 A1 | 8/2006 | Spradlin et al. |
| 2005/0228483 A1 | 10/2005 | Kaplan et al. | 2006/0193890 A1 | 8/2006 | Owens et al. |
| 2005/0228491 A1 | 10/2005 | Snyder et al. | 2006/0193892 A1 | 8/2006 | Furst et al. |
| 2005/0232968 A1 | 10/2005 | Palmaz et al. | 2006/0198869 A1 | 9/2006 | Furst et al. |
| 2005/0233965 A1 | 10/2005 | Schwartz et al. | 2006/0199876 A1 | 9/2006 | Troczynski et al. |
| 2005/0234538 A1 | 10/2005 | Litvack et al. | 2006/0200229 A1 | 9/2006 | Burgermeister et al. |
| 2005/0244459 A1 | 11/2005 | DeWitt et al. | 2006/0200231 A1 | 9/2006 | O'Brien et al. |
| 2005/0251245 A1 | 11/2005 | Sieradzki et al. | 2006/0200233 A1 | 9/2006 | Kujawski |
| 2005/0251249 A1 | 11/2005 | Sahatjian | 2006/0210595 A1 | 9/2006 | Singhvi et al. |
| 2005/0255707 A1 | 11/2005 | Hart et al. | 2006/0212108 A1 | 9/2006 | Tittelbach |
| 2005/0261760 A1 | 11/2005 | Weber | 2006/0222679 A1 | 10/2006 | Shanley et al. |
| 2005/0266039 A1 | 12/2005 | Weber | 2006/0222844 A1 | 10/2006 | Stinson |
| 2005/0266040 A1 | 12/2005 | Gerberding | 2006/0224237 A1 | 10/2006 | Furst et al. |
| 2005/0266041 A1 | 12/2005 | Gerold et al. | 2006/0229711 A1 | 10/2006 | Yan et al. |
| 2005/0267561 A1 | 12/2005 | Jones et al. | 2006/0229713 A1 | 10/2006 | Shanley et al. |
| 2005/0271703 A1 | 12/2005 | Anderson et al. | 2006/0230476 A1 | 10/2006 | Atanasoska et al. |
| 2005/0271706 A1 | 12/2005 | Anderson et al. | 2006/0233941 A1 | 10/2006 | Olson |
| 2005/0276837 A1 | 12/2005 | Anderson et al. | 2006/0241739 A1 | 10/2006 | Besselink et al. |
| 2005/0278016 A1 | 12/2005 | Welsh et al. | 2006/0251701 A1 | 11/2006 | Lynn et al. |
| 2005/0278021 A1 | 12/2005 | Bates et al. | 2006/0259133 A1 | 11/2006 | Sowinski et al. |
| 2005/0281863 A1 | 12/2005 | Anderson et al. | 2006/0264138 A1 | 11/2006 | Sowinski et al. |
| 2005/0283224 A1 | 12/2005 | King | 2006/0271156 A1 | 11/2006 | Ledergerber |
| 2005/0283229 A1 | 12/2005 | Dugan et al. | 2006/0271168 A1 | 11/2006 | Kleine et al. |
| 2005/0287188 A1 | 12/2005 | Anderson et al. | 2006/0271169 A1 | 11/2006 | Lye et al. |
| 2006/0002979 A1 | 1/2006 | Ashammakhi et al. | 2006/0271192 A1 | 11/2006 | Olsen et al. |
| 2006/0009839 A1 | 1/2006 | Tan | 2006/0275554 A1 | 12/2006 | Zhao et al. |
| 2006/0013850 A1 | 1/2006 | Domb | 2006/0276877 A1 | 12/2006 | Owens et al. |
| 2006/0014039 A1 | 1/2006 | Zhang et al. | 2006/0276878 A1 | 12/2006 | Owens et al. |
| 2006/0015175 A1 | 1/2006 | Palmaz et al. | 2006/0276879 A1 | 12/2006 | Lye et al. |
| 2006/0015361 A1 | 1/2006 | Sattler et al. | 2006/0276884 A1 | 12/2006 | Lye et al. |
| 2006/0020742 A1 | 1/2006 | Au et al. | 2006/0276885 A1 | 12/2006 | Lye et al. |
| 2006/0022971 A1 | 2/2006 | Luo et al. | 2006/0280770 A1 | 12/2006 | Hossainy et al. |
| 2006/0025848 A1 | 2/2006 | Weber et al. | 2006/0292388 A1 | 12/2006 | Palumbo et al. |
| 2006/0035026 A1 | 2/2006 | Atanasoska et al. | 2007/0003589 A1 | 1/2007 | Astafieva et al. |
| 2006/0036281 A1 | 2/2006 | Patterson et al. | 2007/0003596 A1 | 1/2007 | Tittelbach et al. |
| 2006/0036311 A1 * | 2/2006 | Nakayama et al. ............ 623/1.15 | 2007/0020306 A1 | 1/2007 | Schultheiss |
| 2006/0038027 A1 | 2/2006 | O'Connor et al. | 2007/0027532 A1 | 2/2007 | Wang et al. |
| 2006/0040388 A1 | 2/2006 | Bromberg et al. | 2007/0032858 A1 | 2/2007 | Santos et al. |
| 2006/0041182 A1 | 2/2006 | Forbes et al. | 2007/0032862 A1 | 2/2007 | Weber et al. |
| 2006/0051397 A1 | 3/2006 | Maier et al. | 2007/0032864 A1 | 2/2007 | Furst et al. |

| Publication No. | Date | Name |
|---|---|---|
| 2007/0034615 A1 | 2/2007 | Kleine |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1 | 2/2007 | Huang et al. |
| 2007/0045252 A1 | 3/2007 | Kleine et al. |
| 2007/0048350 A1 | 3/2007 | Falotico et al. |
| 2007/0050007 A1 | 3/2007 | Kondyurin et al. |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1 | 3/2007 | Hossainy et al. |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1 | 3/2007 | Lee |
| 2007/0077163 A1 | 4/2007 | Furst et al. |
| 2007/0104753 A1 | 5/2007 | Flanagan |
| 2007/0106347 A1 | 5/2007 | Lin |
| 2007/0106363 A1 | 5/2007 | Weber |
| 2007/0123973 A1 | 5/2007 | Roth et al. |
| 2007/0129789 A1 | 6/2007 | Cottone, Jr. et al. |
| 2007/0129792 A1 | 6/2007 | Picart et al. |
| 2007/0134288 A1 | 6/2007 | Parsonage et al. |
| 2007/0135908 A1 | 6/2007 | Zhao |
| 2007/0141106 A1 | 6/2007 | Bonutti et al. |
| 2007/0142897 A1 | 6/2007 | Consigny et al. |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1* | 7/2007 | Weber .......................... 623/1.38 |
| 2007/0156248 A1 | 7/2007 | Marco et al. |
| 2007/0160641 A1 | 7/2007 | Jang |
| 2007/0168016 A1 | 7/2007 | Gronemeyer et al. |
| 2007/0173923 A1 | 7/2007 | Savage et al. |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1 | 10/2007 | Weber et al. |
| 2007/0250155 A1 | 10/2007 | Simpson |
| 2007/0250156 A1 | 10/2007 | Palmaz |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1 | 12/2007 | Gale et al. |
| 2007/0281117 A1 | 12/2007 | Kaplan et al. |
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0004691 A1 | 1/2008 | Weber et al. |
| 2008/0031765 A1 | 2/2008 | Gerold et al. |
| 2008/0033522 A1 | 2/2008 | Grewe et al. |
| 2008/0033530 A1 | 2/2008 | Zberg et al. |
| 2008/0033531 A1 | 2/2008 | Barthel et al. |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1 | 2/2008 | Chen et al. |
| 2008/0051872 A1 | 2/2008 | Borck |
| 2008/0051881 A1* | 2/2008 | Feng et al. .................... 623/1.39 |
| 2008/0057105 A1 | 3/2008 | Atanasoska et al. |
| 2008/0058919 A1 | 3/2008 | Kramer-Brown et al. |
| 2008/0058921 A1 | 3/2008 | Lindquist |
| 2008/0058923 A1 | 3/2008 | Bertsch et al. |
| 2008/0069854 A1 | 3/2008 | Xiao et al. |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1* | 3/2008 | Weber et al. .................. 623/1.15 |
| 2008/0071353 A1 | 3/2008 | Weber et al. |
| 2008/0071355 A1 | 3/2008 | Weber et al. |
| 2008/0071357 A1 | 3/2008 | Girton et al. |
| 2008/0071358 A1 | 3/2008 | Weber et al. |
| 2008/0082162 A1 | 4/2008 | Boismier et al. |
| 2008/0086199 A1 | 4/2008 | Dave et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1* | 6/2008 | Scheuermann et al. ..... 623/1.42 |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1* | 8/2008 | Allen et al. ................... 623/1.11 |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1* | 10/2008 | Shastri et al. .................... 606/33 |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0269872 A1 | 10/2008 | Lootz et al. |
| 2008/0288048 A1 | 11/2008 | Rolando et al. |
| 2008/0290467 A1 | 11/2008 | Shue |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |

| Publication No. | Date | Name |
|---|---|---|
| 2009/0018639 A1 | 1/2009 | Kuehling |
| 2009/0018647 A1 | 1/2009 | Benco et al. |
| 2009/0018648 A1 | 1/2009 | Wittchow |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1* | 2/2009 | Blaha et al. ............. 623/1.46 |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1* | 4/2009 | Wang ..................... 623/1.15 |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1* | 5/2009 | Swetlin et al. ............. 604/8 |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1* | 6/2009 | Miller et al. ............. 623/1.15 |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1* | 11/2009 | Weber ..................... 623/1.46 |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishnan et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |
| 2010/0047324 A1 | 2/2010 | Fritz et al. |
| 2010/0049146 A1 | 2/2010 | Nielsen et al. |
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |

FOREIGN PATENT DOCUMENTS

| | | |
|---|---|---|
| AU | 2003 203 722 | 11/2003 |
| CA | 2 235 031 | 10/1998 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| DE | 2 139 535 | 1/2010 |
| EP | 0 006 544 | 6/1979 |
| EP | 0 337 035 | 11/1993 |
| EP | 0 923 389 | 7/1998 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 0 951 877 | 6/2004 |
| EP | 1 260 214 | 6/2004 |
| EP | 0 875 218 | 2/2005 |
| EP | 1 733 746 | 12/2006 |
| EP | 1 752 167 | 2/2007 |
| EP | 1 835 042 | 9/2007 |
| EP | 1 750 780 | 10/2007 |
| EP | 1 653 885 | 4/2009 |
| EP | 1 703 858 | 10/2009 |
| EP | 1 883 380 | 3/2010 |
| EP | 2 189 169 | 5/2010 |

| | | |
|---|---|---|
| RU | 2 218 242 | 12/2003 |
| WO | 93/04118 | 3/1993 |
| WO | 97/11724 | 4/1997 |
| WO | 98/29025 | 7/1998 |
| WO | 98/48851 | 11/1998 |
| WO | 99/33410 | 7/1999 |
| WO | 99/47077 | 9/1999 |
| WO | 99/64580 | 12/1999 |
| WO | 00/25841 | 5/2000 |
| WO | 00/48660 | 8/2000 |
| WO | 00/51136 | 8/2000 |
| WO | 00/54704 | 9/2000 |
| WO | 00/66190 | 11/2000 |
| WO | 01/49338 | 7/2001 |
| WO | 01/78906 | 10/2001 |
| WO | 01/80920 | 11/2001 |
| WO | 01/87371 | 11/2001 |
| WO | 02/45764 | 6/2002 |
| WO | 02/47739 | 6/2002 |
| WO | 02/053202 | 7/2002 |
| WO | 03/002243 | 1/2003 |
| WO | 03/013396 | 2/2003 |
| WO | 03/035131 | 5/2003 |
| WO | 03/035134 | 5/2003 |
| WO | 03/035278 | 5/2003 |
| WO | 03/063733 | 8/2003 |
| WO | 03/094990 | 11/2003 |
| WO | 2004/029313 | 4/2004 |
| WO | 2004/043292 | 5/2004 |
| WO | 2004/093643 | 11/2004 |
| WO | 2005/025449 | 3/2005 |
| WO | 2005/065576 | 7/2005 |
| WO | 2005/079335 | 9/2005 |
| WO | 2005/110395 | 11/2005 |
| WO | 2005/118019 | 12/2005 |
| WO | 2006/008739 | 1/2006 |
| WO | 2006/060033 | 6/2006 |
| WO | 2006/060534 | 6/2006 |
| WO | 2006/065356 | 6/2006 |
| WO | 2006/077154 | 7/2006 |
| WO | 2006/080381 | 8/2006 |
| WO | WO 2006/097503 | 9/2006 |
| WO | 2006/108065 | 10/2006 |
| WO | WO 2006/104644 | 10/2006 |
| WO | 2007/005806 | 1/2007 |
| WO | 2007/013102 | 2/2007 |
| WO | 2007/018931 | 2/2007 |
| WO | 2007/024552 | 3/2007 |
| WO | 2007/035791 | 3/2007 |
| WO | 2007/079363 | 7/2007 |
| WO | 2007/079636 | 7/2007 |
| WO | 2007/082147 | 9/2007 |
| WO | 2007/139668 | 12/2007 |
| WO | 2008/003450 | 3/2008 |
| WO | 2008/062414 | 5/2008 |
| WO | 2008/092436 | 8/2008 |
| WO | 2008/106271 | 9/2008 |
| WO | 2008/117315 | 10/2008 |
| WO | 2008/118606 | 10/2008 |

OTHER PUBLICATIONS

Gabrielli, Claude. "Use and Applications of Electrochemical Impedance Techniques". 1997, 1-102.
Mansfeld, Florian. "Analysis and Interpretation of EIS Data for Metals and Alloys". 1999, 1-77.
Marijan et al. "Surface Modification of Stainless Steel-304 Electrode. 2. An Experimental Comparative Study of Electrochemically, Hydrothermally and Chemically Modified Oxide Films." CCACAA, 1999, 72(4) 751-761.
Purushothaman et al. "Reducing Mass-Transport Limitations by Application of Special Pulsed Current Modes". Journal of the Electrochemical Society. 152 (4), 2005, J33-J39.
Authorized officer Wolfgang Urack, International Search Report/ Written Opinion in PCT/US2009/43326 mailed Aug. 6, 2009, 9 pages.
U.S. Appl. No. 10/849,742, filed May 20, 2004, Chen et al.
U.S. Appl. No. 60/826,002, filed Sep. 18, 2006, Girton et al.
U.S. Appl. No. 60/845,136, filed Sep. 15, 2006, Weber and Atanasoska.
U.S. Appl. No. 60/862,318, filed Oct. 20, 2006, Atanasoska et al.
"Best of the ACC Scientific Session 2002," Rev. Cardiovasc. Med., 2002, 3(2):85-104.
"Chapter 2: Corrosion Theory and Corrosion Protection," EM 1110-2-3400, 1995, 8 pages.
"Galvanic cell" printout from wikipedia, 5 pages, printed on Aug. 16, 2010.
"Galvanicc corrosion," http://www.corrosion-doctors.org/aircraft/galvdefi.htm, 3 pgs., printed Oct. 28, 2005.
"Galvanic series" printout from Wikipedia, p. 1 of 2, printed Oct. 28, 2005.
Aaltonen, "Atomic Layer Deposition of Noble Metal Thin Films," University of Helsinki, Apr. 8, 2005, pp. 1-71.
Aghion et al., "Newly Developed Magnesium Alloys for Powertrain Applications," JOM, 2003, p. 30.
Albion Research Notes, Newsletter, Oct. 1994, 3(4): 1-4.
Anand et al., "Ion-exchange resins: carrying drug delivery forward," DDT, 2001, 6: 905-914.
Anderson et al., "A new conductive polymer as a replacement for chrome conversion coating," 2003 Aerospace Coatings Removel and Coatings Conference,May 20-22, 2003, Colorado Springs, CO, 7 pages.
Andión et al., "Corrosion behaviour at the interface of steel bars embedded in cement slurries Effect of phenol polymer coatings," Corrosion Science, 2002, 44:2805-2816.
Antipov et al., "Polyelectrolyte Multilayer Capsule Permeability Control," Colloids and Surfaces A: Physiochem. Eng. Aspects, 2002, 198-200, 535-541.
Antipov et al., "Polyelectrolyte Multilayer Capsules as Vehicles with Tunable Permeability", Advances in Colloid and Interface Science, 2004, 111: 49-61.
Arts et al., "Polyphenols and disease risk in epidemiologic studies," Am. J. Clin. Nutr., 2005, 81:317S-325S.
Artyukhin et al., "Layer-by-Layer Electrostatic Self-Assembly of Polyelectrolyte Nanoshells on Individual Carbon Nanotube Templates," Langmuir, 2004, 20:1442-1448.
Ashtari et al. "An efficient method for recovery of target ssDNA based on amino-modified silica-coated magnetic nanoparticles" Talanta, 2005, 67:548-554.
Atta, "Electrochemical synthesis, characterization and some properties of a polymer derived from thioflavin S.," European Polymer Journal, 2005, 41: 3018-3025.
Australian Government, Department of Health and Aging, "Horizon Scanning Technology Prioritising Summary-Biodegradable stents for coronary artery disease," Australia and New Zealand Horizon Scanning Network(ANZHSN), Aug. 2007, pp. 1-13.
Authorized Officer Athina Nickitas-Etienne, International Preliminary Report on Patentability in PCT/US07/78449 mailed Mar. 26, 2009, 9 pages.
Authorized Officer Athina Nickitas-Etienne, International Preliminary Report on Patentability in PCT/US07/79841 mailed Apr. 30, 2009, 7 pages.
Authorized officer Athina Nickitas-Etienne, International Preliminary Report on Patentability in PCT/US08/86639 mailed Jun. 24, 2010, 2 pages.
Authorized Officer Cecilia Giel-Barragan Ramos, International Search Report/Written in PCT/US07/79841 mailed Feb. 4, 2009, 11 pages.
Authorized Officer Elisabeth Reinecke, International Search Report/ Written Opinion in PCT/US07/60137 mailed Jul. 27, 2007, 20 pages.
Authorized Officer Joëlle Gerber, International Search Report/Written Opinion in PCT/US07/78450 mailed Nov. 19, 2008, 17 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
International Search Report/Written Opinion in PCT/US2008/86639 mailed Feb. 23, 2010, 8 pages.
Authorized Officer Simin Baharlou, International Preliminary Report on Patentability in PCT/US07/66568 mailed Oct. 23, 2008, 10 pages.

Authorized Officer Simin Baharlou, International Preliminary Report on Patentability in PCT/US07/75072 mailed Feb. 12, 2009, 9 pages.
Authorized Officer Trudy Hinterwimmer, International Search Report/Written Opinion in PCT/US07/78412 mailed Mar. 3, 2008, 10 pages.
Authorized Officer Trudy Hinterwimmer, International Search Report/Written Opinion in PCT/US09/49422 mailed Aug. 24, 2009, 10 pages.
Authorized Officer Véronique van Loon-Mégard, International Search Report/Written Opinion in PCT/US08/75976 mailed Nov. 25, 2008, 20 pages.
Babapulle and Eisenberg, "Coatred stents for their prevention of restenosis: Part II," *Circulation*, 2021, 106: 2849-2866.
Bach et al., "Corrosion, Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Balasubramanian et al. "Dispersion and Stability Studies of Resorcinarene-Encapsulated Gold Nanoparticles." *Langmuir*, 2002, 1676-3681.
Bao, Y. et al. "Preparation of functionalized and gold-coated cobalt nanocrystals for biomedical applications." *Journal of Magnetism and Magnetic Materials*, 2005, 293:15-19.
Baurschmidt et al., "The Electrochemical Aspects of the Thrombogenicity of a Material," *J. Bioengineering*, 1977, 1:261-278.
Bekesi et al., "Efficient Submircon Processing of Metals with Femto," *Appl. Phys. A.*, Published Oct. 25, 2002, pp. 355-357.
Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.
Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.
Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.
Bernkop-Schnurch, "Chitosan and its derivatives: potential excipients for peroral peptide delivery systems," *International J. of Pharmaceutics*, 2000, 194: 1-13.
Berry et al., "Functionalisation of magnetic nanoparticles for applications in biomedicine," *J. Phys. D: Appl. Phys.*, 2003, 36:R198-R206.
Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.
Blanusa et al., "Chelators as Antidotes of Metal Toxicity Therapeutic and Experimental Aspects," *Current Medicinal Chemistry*, 2005, vol. 12, pp. 2771-2794.
Bolz et al., "Effect of smooth, porous and fractal surface structure on the properties of an interface," *J. Materials Science: Materials in Medicine*, 1995, 844-848.
Bosiers et al., "Absorbable Metal stent for CLI in Infrapopliteal lesions: 1 year results," *CX 2005 Global Endovascular Forum*, Apr. 2005, pp. 1-23.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.
Brückner et al., "Metal plasma immersion ion implantation and deposition (MPIIID): chromium on magnesium," *Surface and Coatings Technology*, 1998, 103-104, pp. 227-230.
Brunatto and Muzart, "Influence of the gas mixture flow on the processing parameters of hollow cathode discharge ion sintering," *J. Phys. D.: Appl. Phys.*, 2007, 40: 3937-3944.
Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Buescher et al., "Characterization of Wet-Chemically Nanostructured Stainless Steel Surfaces," *Mat. Res. Soc. Symp. Proc.*, 2001, 676:1-6.
Caruso et al., "Ultrathin Molybdenum Polyoxometalate-Polyelectrolyte Multilayer Films," *Langmuir*, 1998, 14:3462-3465.
Casan-Pastor et al., "Polyoxometalates: From Inorganic Chemistry to Materials Science," *Frontiers in Bioscience*, 2004, 9:1759-1770.
Chaieb et al , "Inhibition of the corrosion of steel in 1 M HCl by eugenol derivatives," *Applied Surface Science*, 2005, 246:199-206.
Chang et al., "Effect of Heat Treatment on Corrosion and Electrochemical behavior of Mg-3Nd-0.2Zn-0.4Zr (wt. %) alloy," *Science Direct, Electrochimica Acta* 52, 2007, 3160-3167.
Chang et al., "Templated sythesis of Gold-iron Alloy nanoparticles using pulsed laser deposition," *Nanotechnology*, vol. 17, 2006, pp. 5131-5135.
Changwen et al., "Polyoxometalate-based organic-inorganic hybrid materials," 2004, *Sol-Gel*, p. 1.
Chen et al., "Laser Cladding of Mg20A18o Powder on ZM5 Magnesium Alloy," *Engineering, Science and Technology*, 2007, vol. 42, No. 2, pp. 130-136.
Cheng et al., "Electrogeneration and electrochemical properties of hybrid materials: polypyrrole doped with polyoxometalates $PW_{12-x}Mo_xO_{40}^{3-}$ (x=0,3,6,12)," *Synthetic Metals*, 2002, 129: 53-59.
Cho et al., "Gold-coated iron nanoparticles: a novel magnetic resonance agent for $T_1$ and $T_2$ weighted imaging," *Nanotechnology*, vol. 17, 2006, pp. 640-644.
Chou et al., "Electrochemical treatment of mouse and rat fibrosarcomas with direct current," *Bioelectromagnetics*, 1997, 18:14-24.
Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.
Conolly et al., "X-Ray microtomography studies of localized corrosion and transitions to stress corrosion cracking," *Materials Science and Technology*, 2006, vol. 22, No. 9, pp. 1076-1085.
Costa et al., "The effect of the magnetic field on the corrosion behavior of Nd-Fe-B permanent magnets." *Journal of Magnetism and Magnetic Materials*, 278, 2004, pp. 348-358.
Damen et al., "Paclitaxel esters of malic acid as prodrugs with improved water solubility," *Bioorganic & Medicinal Chemistry*, 2000, 8: 427-432.
Damiani et al., "Vasorelaxant effects on eugenol on rat thoracic aorta," *Vascular Pharmacol.*, 2003, 40:59-66.
Davies, "Changing the salt, changing the drug," *The Pharmaceutical Journal*, 2001, 266: 322-323.
De Geest et al., "Self-rupturing Microcapsules," *Adv. Mater.*, 2005, vol. 17, pp. 2357-2361.
de Witte, "Analysis of the principal component of external casing corrosion in deep wells," *J. Appl. Electrochem.*, 1985, 15: 325-334.
Dexter, "Galvanic Corrosion," MAS Note, University of Delaware Sea Grant Marine Advisory Service, 2003.
Di Mario et al., "Drug-eluting bioabsorbable magnesium stent," *J. Interventional Cardiol.*, 2004, 17(6):391-395.
Di Mario et al., "Moonlight: a controlled registry of an iridium oxide-coated stent with angiographic follow-up," *Int. J. Cardiol.*, 2004, 95:329-331.
Dowling et al., "Anti-bacterial silver coatings exhibiting enhanced activity through the addition of Platinum," *Surf. & Coatings Tech.*, 2003, 163-164:637-640.
Duncan et al., "Polymer-drug conjugates, PDEPY and PELT: basic principles for design and transfer from the laboratory to clinic," *Journal of Controlled Release*, 2001, 74: 135-146.
Duncan, "The dawning era of polymer 360 therapeutics," *Nature Reviews/Drug Discovery*, 2003, 2: 347-360.
Duygu, "*Controlled Release Systems*," http://www.biomed.metu.edu.tr/courses/term_papers/contr-rel-sys_duygu.htm (Dec. 30, 2005).
Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

European Examiner Marie-France Weiss, International Preliminary report on Patentability received in PCT/US2007/078417, mailed Mar. 26, 2009, 8 pages.

International Preliminary Report on Patentability, received in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.

International Preliminary Report on Patentability in PCT/US07/78411 mailed Feb. 4, 2009, 8 pages.

International Preliminary Report on Patentability in PCT/US07/78412 mailed Apr. 2, 2009, 7 pages.

International Preliminary Report on Patentability in PCT/US07/78505 mailed Mar. 26, 2009, 7 pages.

International Preliminary Report on Patentability in PCT/US07/78450 mailed Mar. 26, 2009, 7 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Farhat et al., "Corrosion Control Using Polyelectrolyte Multilayers," *Electrochemical and Solid State Letters*, 2002, 5(4):B13-B15.

Feng et al., "Sonochemical preparation of photochromic nanocomposite thin film based on polyoxometalates well dispersed in polyacrylamide,"*Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Hournal of Modern Physics B*, vol. 17, Nos. 8 & 9, 2003, pp. 1601-1607.

Ferrando, "Review of Corrosion and Corrosion Control of Magnesium Alloys and Composites," *J. Mater. Eng.*, 1989, 11:299-313.

Fischer et al., "Determination of in-vivo corrosion rates of degradable implants by SR-microtomography," date unknown, pp. 1-2.

Fischer et al., "Hydrogen in magnesium alloys and magnesium interfaces: preparation, electronic properties and interdiffusion," *J. Less-Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.

Fraunhofer IIS—Poster (German), "Prinzip der hochauflosenden Comptuertomographie," 2009, 1 page.

Frei, "On the Role of Vitamin C and Other Antioxidants in Atherogenesis and Vascular Dysfunction,"*Proceedings—Society for Experimental Biology and Medicine*, 1999, 222:196-204.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests,"*Journal of Dental Research*, 1980, vol. 59, pp. 689-707.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.

Griffiths et al., "Future devices: bioabsorbable stents," *Br. J. Cardiol.* (*Acute & Interventional Cardiology*), 2004, 11:AIC80-AIC84.

Grube, "Bioabsorbable Stents—The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Guo et al., "Manipulation of single-wall carbon nanotubes into aligned molecular layers," *Chem. Phys. Lett.*, 2002, 362:314-318.

Guo et al., "Multi-layer LB films of single-wall carbon nanotubes," *Physica B*, 2002, 323:235-236.

Gupta et al., "Nanometer spaced electrodes using selective area atomic layer deposition," *Applied Physics Letters*, vol. 90, 2007, pp. 1-4.

Gurib-Fakim, "Medicinal plants: Traditions of yesterday and drugs of tomorrow," *Molecular Aspects of Medicine*, 2006, 27:1-93.

Haenzi et al., "Design strategy for microalloyed ultra-ductile Mg alloys," *Phil. Mag. Letters*, 89(6):377-390.

Haenzi et al., "Design strategy for new biodegradable Mg-Y-Zn alloys for medical applications," *Int. J. Mat. Res.*, 2009, 100: 1127-1136.

Haenzi et al., "On the biodegradation performance of an Mg-Y-RE alloy with various surface conditions in simulated body fluid," *Acto Biomat.*, 2009, 5: 162-171.

Haferkamp et al., "Magnesium-Base-Alloys as Implant-Material Steps to the Production of Thin Components," *Magnesium*, 2000, 159-164.

Hamu et al., "Influence of Si, Ca and Ag addition on corrosion behavior of new wrought Mg-Zn alloys," 2006, 22(10): 1213-1218.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg-Y-Zn alloys for medical applications,"*Int. J. Mat. Res.*, vol. 100, 2009, pp. 1127-1136.

Hänzi et al., "On the biodegradation performance of an Mg-Y-Re alloy with various surface conditions in simulated body fluid," *Acta Biomaterialia*, vol. 5, 2009, pp. 162-171.

Haque et al. "Bioabsorption Qualities of Chitosan-absorbable Vascular Templates," *Current Surgery*, 2001, 58(1): 77-80.

Hau et al., "Surface-Chemistry Technology for Microfluidics," *J. Micromech. Microeng.*, 2003.13:272-278.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Developments in metallic biodegradable stents," *Acta Biomaterialia*, 2010, 6: 1693-1697.

Hermawan et al., "Degradable metallic biomaterials: Design and development of Fe-Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, 2007, 15-17:113-118.

Hermawan et al., "Development of Degradable Fe-35Mn Alloy for Biomedical Application," *Advanced Material Research*, 2007, 15-17:107-112.

Hermawan et al., "Fe-Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, 51(1):38-45.

Heublein et al., "Biocorrosion of magnesium alloys: a new principle in cardiovascular implant technology?" *Heart*, 2003, 89:651-656.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Local Tissue Engineering by Biocorrosion Vision or Reality?"*The American Journal of Cardiology, TCT Abstracts/Poster*, Oct. 16, 2000.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Huang et al., "A Review on Polymer Nanofibers by Electro-spinning and their Applications in Nanocomposites," 2003, 63:2223-2253.

Hutten, A. et al. "Ferromagnetic FeCo nanoparticles for biotechnology". (2005) *Journal of Magnetism and Magnetic Materials* 293:93-101).

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of ofλFe2O3 nanoparticles with aminopropylsilyl groups and interparticle linkage with with a,w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability in PCT/US07/60137 mailed Jul. 17, 2008, 7 pages.

International Preliminary Report on Patentability in PCT/US07/73839 mailed Apr. 2, 2009.

International Preliminary Report on Patentability in PCT/US07/78429 mailed Apr. 2, 2009.

International Preliminary Report on Patentability in PCT/US07/78475 mailed Aug. 26, 2009, 8 pages.

International Preliminary Report on Patentability received in PCT/US2007/078479, mailed Mar. 26, 2009, 8 pages.

International Search Report/Written Opinion in PCT/US09/046750 mailed Jul. 20, 2010, 14 pages.

International Search Report and Written Opinion in PCT/US07/78449, mailed Jan. 13, 2009, 15 pages.

International Search Report and Written Opinion in PCT/US07/78475, mailed Feb. 4, 2009, 14 pages.

International Search Report and Written Opinion in PCT/US07/78476, mailed Jan. 28, 2009, 29 pages.

International Search Report and Written Opinion mailed Jan. 25, 2008 in PCT/US07/75072, 14 pages.

International Search Report and Written Opinion received in PCT/US2007/078417, mailed Jan. 22, 2009, 18 pages.

International Search Report and Written Opinion received in PCT/US2007/078479, mailed Dec. 30, 2008, 12 pages.

International Search Report for PCT/US05/16600 mailed May 4, 2006, 4 pages.

International Search Report for PCT/US07/66568 dated Oct. 8, 2007, 15 pages.

International Search Report from PCT/US 03/20215, mailed Nov. 11, 2003, 4 pages.

International Search Report/Written Opinion in PCT/US07/73839 mailed Apr. 16, 2008, 16 pages.

International Search Report/Written Opinion in PCT/US07/78411 mailed Mar. 6, 2008, 12 pages.

International Search Report/Written Opinion in PCT/US07/78429 mailed 28 Mar. 2008, 14 pages.

International Search Report/Written Opinion in PCT/US07/78505 mailed 4 Mar. 2008, 10 pages.

International Search Report/Written Opinion in PCT/US2007/078407, mailed Mar. 26, 2008, 10 pages.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11A1-0.5Zn matrix composite," *Materials Science and Engineering A*, 2004, 381: 223-229.

Jiang, "A review of wet impregnation—An alternative method for the fabrication of high performance and nano-structured electrodes of solid oxide fuel cells," *Materials Science and Engineering A*, 2006, 418:199-210.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kean and Davies, "Cathodic Protection," 7 pages, 1981; http://www.npl.co.uk/upload/pdf/cathodic_protection.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kokubo et al., "How useful is SBF in predicting in vivo bone bioactivity?" *Biomaterials*, 2006, 27: 2907-2915.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydries: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

LaFont, "Arterial Remodeling Technologies: Bioresorbable Stents," *Euro PCR09*, 2009, pp. 1-28.

Lambert et al., "Inhibition of carcinogenesis by polyphenols: evidence from laboratory investigations," *Am. J. Clin. Nutr.*, 2005, 81(suppl):284S-291S.

Lee et al., "Retentive and compressive strengths of modified zinc oxide-eugenol cements," *J. Dentistry*, 2000, 28:69-75.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-*co*-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maier et al., "High concentrations of magnesium modulate vascular endothelial cell behaviour in vitro," *Biochim Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-August-Universität Göttingen, 134 pages.

*Methods in Cell Biology (Cell Death)*, vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Middleton and Tipton, "*Synthetic Biodegradable Polymers as Medical Devices*," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterials*, 1992, 13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81 (suppl):277S-283S.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Naderi et al., "Effect of some volatile oils on the affinity of intact and oxidized low-density lipoproteins for adrenal cell surface receptors," *Mol. Cell. Biochem.*, 2004, 267:59-66.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ou et al., "Protective effects of eugenol against oxidized LDL-induced cytotoxicity and adhesion molecule expression in endothelial cells," *Food Chem. Toxicol.*, 2006, 44:1485-1495.

Ouerd et al., "Reactivity of Titanium in Physiolgoical Medium-I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Park et al., "Microstructural change and precipitation hardening in melt-spun Mg-X-Ca alloys," *Science and Technology of Advanced Materials*, 2001, 2:73-78.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Peuster et al., "Are resorbable implants 116 about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.

Prasse et al., "Electric Anisotropy of Carbon Nanofibre/Epoxy Resin Composites Due to Electric Field Induced Alignment," *Composites Science and Technology*, 2003, 63:1835-1841.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Ratnam et al., "Role of antioxidants in prophylaxis and therapy: A pharmaceutical perspective," *J. Controlled Release*, 2006, 113:189-207.

Reece et al., "Metal transport studies on inherently conducting polymer membrances containing cyclodextrin dopants," *Journal of Membrane Science*, 2005, 249: 9-20.

Remskar et al., "Self-Assembly of Subnanometer-Diameter Single-Wall $MoS_2$ Nanotubes," *Science*, 2001, 292:479-481.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting Stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schauer et al., "Protection of iron against corrosion with polyaniline primers," *Progress in Organic Coatings*, 1998, 33: 20-27.

Schetky, "Shape Memory Alloys," *Encyclopedia of Chemical Technology* (3rd ed.), 1982, John Wiley & Sons, 20:726.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pages 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shaw, "Corrosion Resistance of Magnesium Alloys," *ASM Handbook vol. 13A: Corrosion: Fundamentals, Testing, and Protection*. 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shi et al., "A novel electrically conductive and biodegradable composite made of polypyrrole nanoparticles and polylactide," *Biomaterials*, 2004, 25:2477-2488.

Shieh et al. "Aqueous dispersions of magnetite nanoparticles with NH3 surfaces for magnetic manipulations of biomolecules and MRI contrast agents" *Biomaterials*, 2005 26: 7183-7191.

Shin, "Experimental Characterization of Electrospinning. the Electrically Forced Jet and Instabilities," *Polymer*, 2001, 42:9955-9967.

Sieber, et al., "Investigations on the passivity of iron in borate and phosphate buffers, pH 8.4," *Corrosion Science*, vol. 48, 2006, pp. 3472-3488.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Song et al., "Galvanic corrosion of magnesium alloy AZ91D in contact with an aluminium alloy, steel and zinc," *Corrosion Science*, 2004, 46:955-977.

Soto et al., "Amporphous magnesium nitride films produced by reactive pulsed lasar deposition," Journal of Non-Crystalline Solids, 2004, 342: 65-69.

Stoclet et al., "Vascular protection by dietary polyphenols," *Eur. J. Pharmacol.*, 2004, 500:299-313.

Stoner et al., "The mechanism of low frequency a.c. Electrochemical Disinfection," *Bioelectrochemistry and Bioenergetics*, 1982, 9:229-243.

Straumal et al., "Vacuum arc deposition of protective layers on glass and polymer," *Thin Solid Films*, 2001, 383:224-226.

Su et al., "Photoacoustic imaging of coronary artery stents," *Optics Express*, vol. 17, No. 22, Oct. 26, 2009, pp. 1-8.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules and Templated on Melamine Formaldehyde and Carbonate Cores," *Macromol. Chem. Phys.*, 2004, 205:530-535.

Sun et al., "Fabrication of a multilayer film electrode containing porphyrin and its application as a potentiometric sensor of iodide ion," *Talanta*, 1998, 46: 15-21.

Suslick et al., "The photochemistry of chromium, manganese, and iron porphytin complexes," J. Chem., 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefügemerkmalen" *Druckguss*, Apr. 2009, pp. 1-5.

Van Alst, "Potential conflicts of interest," *Euro PCR09*, 2009, pp. 1-22.

Vermette et al., "Immobilized Liposome Layers for Drug Delivery Applications," *J. Controlled Release*, 2002, 80:179-195.

Virtanen et al., "Electrochemical Behavior of Fe in Phosphate Solutions Studied by in Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$Nanowires," *Nanotechnology*, 2004, 15:635-638.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to theFuture, *Euro PCR09*, 2009, pp. 1-16.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membranes," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Wang et al., "Characterisation of Severely Deformed Austenitic Stainless Stell Wire," *Materials Science and Technology*, 21(11):1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

Weiss et al., "Pyrrole derivatives for electrochemical coating of metallic medical devices," *J. Polymer Science, Part A: Polymer Chemistry*, 2004, 42: 1658-1667.

White and Slade, "Polymer electrodes doped with heteropolymetallates and their use within solid-state supercapacitors," *Synthetic Metals*, 2003, 139: 123-131.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology,"*Herz*, 2002, 27(6):518-526.

Wilcox, "Biodegradable Technology: Medtronic Biodegradable Stent Program," *Euro PCR09*, 2009, pp. 1-25.

Williamson and Manach, "Bioavailability and bioefficacy of polyphenols in humans. II. Review of 93 intervention studies," *Am. J. Clin. Nutr.*, 2005, 81(suppl):243S-255S.

Windecker et al., "Biolimus-eluting stent with biodegradable polymer versus sirolimus-eluting stent with durable polymer for coronary revascularisations (Leadrers): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In vitro and in vivo corrosion measurements of magnesium alloys," *Biomaterials*, 2006, 27:1013-1018.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Yamaguchi et al., "Mg2Si Coating Technology on Magnesium Alloys to Improve Corrosion and Wear Resistance", *JOM*, 2004, p. 343.

Ye et al., "In situ synthesis of AlN particles in Mg-Al alloy by $Mg_3$-$N_2$ addition," *Materials Letters*, 2004, 58:2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys,"*Scripta mater.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

*Zeta Potential-An Introduction in 30 Minutes, Technical Note*, http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Improving multilayer films endurance by photoinduced interaction between Dawson-type polyoxometalate and diazo resin," *Materials Chemistry and Physics*, 2005, 90:47-52.

Zhang et al., "Natural Polyelectrolyte Films Based on Layer-by-Layer Deposition of Collagen and Hyaluronic Acid," *Biomaterials*, 2005, 26:3353-3361.

Zhang et al., "Ways for fabricating stable a layer-by layer self-assemblies: combined ionic self-assembly and post chemical reaction," *Colloids and Surfaces A: physiochemical and Engineering Aspects*, 2002, pp. 198-200, 439-442.

Zheng, "Symposium on Biodegradable/Biocorroded metallic materials," Nov. 24, 2009, pp. 1-74.

Zhou et al., "Drug-loaded, Magnetic, hollow silica nanocomposites for nanomedicine," *Nanomedicine: Nanotechnology, Biology and Medicine*, 2005, 1:233-237.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: in Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Zucchi et al., "Influence of a silane treatment on the corrosion resistance of a WE43 magnesium alloy," *Surface Coatings Technol.*, 2006, 200:4136-4143.

International Search Report and Written Opinion from PCT/US09/043591, mailed Jun. 30, 2010, 10 pages.

International Search Report from PCT/US07/005671, mailed Jun. 2, 2008, 10 pages.

Ma et al , "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," Colloids and Surfaces A: Physiochem. Eng. Aspects, 2006, 273: 16-23.

International Preliminary Report on Patentability from PCT/US08/75976 dated Mar. 25, 2010, mailed Nov. 25, 2008, 8 pages.

US 6,533,715, 03/2003, Hossainy et al. (withdrawn)

* cited by examiner

ENDOPROSTHESES

TECHNICAL FIELD

This invention relates to endoprostheses, and more particularly to bioerodible endoprostheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721, the entire contents of which is hereby incorporated by reference herein.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

Passageways containing endoprostheses can become re-occluded. Re-occlusion of such passageways is known as restenosis. It has been observed that certain drugs can inhibit the onset of restenosis when the drug is contained in the endoprosthesis. It is sometimes desirable for an endoprosthesis-contained therapeutic agent, or drug to elute into the body fluid in a predetermined manner once the endoprosthesis is implanted.

SUMMARY

There is described an endoprosthesis that includes a body defining a flow passage therethrough and is capable of maintaining patency in a blood vessel. The body includes iron or an alloy thereof. The body has a nano-structured surface comprising iron oxide in which the individual nano-structures have a height to thickness aspect ratio of at least 5:1.

In some embodiments, the height to thickness aspect ratio is between 10:1 and 20:1. For example, the height of each individual nano-structure can be between about 50 nm and about 500 nm. In some embodiments, the individual nano-structures can have a flake structure each having a width of at least twice the thickness. For example, the thickness of each individual flake nano-structure can be between about 5 nm to 50 nm and the width of each individual flake nano-structure can be between about 100 nm to 500 nm. In other embodiments, the individual nano-structures can have a rice grain structure. For example, an individual rice grain nano-structure can have a diameter of between about 5 nm to 50 nm. In some embodiments, an average separation distance between adjacent individual nano-structures can be between about 1 nm and 50 nm.

The nano-structured surface of the body can also be described by its roughness characteristics and/or resistance to corrosion. For example, the surface of the body can have a $S_{dr}$ of between 120 and 200. A nano-structured surface can have a resistance to corrosion of less than 5 Kohms (e.g., about 2 Kohms).

In some embodiments, the endoprosthesis can further include a polymer coating over at least a portion of the nano-structured surface. For example, the polymer coating can include a co-block polymer of polyglutamic acid and one or more of the following polymers: poly(ethylene oxide), polycaprolactam, poly(lactic-co-glycolic acid), and polysaccharides. For example, the polymer can include a co-block polymer of polyglutamic acid and a non-ionic polysaccharide (e.g., pullulan). In some embodiments, the polymer coating can be a drug eluting coating that includes a therapeutic agent.

The endoprosthesis can, in some embodiments, be bioerodible. For example, the body can include a bioerodible metal, such as pure iron. A coating, if present, can also be a bioerodible polymer.

The endoprosthesis can, in some embodiments, be a stent.

In another aspect, an endoprosthesis is described that includes a body defining a flow passage therethrough that is capable of maintaining patency in a blood vessel. The body includes iron or an alloy thereof and has a surface comprising iron oxide. The endoprosthesis also includes a coating over the surface that includes a co-block polymer of polyglutamic acid.

In some embodiments, the co-block polymer of polyglutamic acid can be a co-block polymer of polyglutamic acid and of a polysaccharide. The polysaccharide can be a non-ionic polysaccharide such as pullulan.

The endoprosthesis can, in some embodiments, be bioerodible. For example, the body can include a bioerodible metal, such as pure iron, and the coating can also be a bioerodible polymer.

The endoprosthesis can, in some embodiments, be a stent.

In another aspect, a method of producing an endoprosthesis is described. The method includes exposing a portion of an endoprosthesis, or a precursor thereof, to an electrolytic solution and applying a plurality of current pulses to the endoprosthesis. The endoprosthesis includes iron or an alloy thereof. The application of the current pulses to the endoprosthesis while exposed to the electrolytic solution creates a nano-structured surface on the endoprosthesis having a plurality of individual nano-structures having a height to thickness aspect ratio of at least 5:1.

In some embodiments, the applied current pulses can include cathodic pulses, anodic pulses, or a combination thereof. The applied current pulses can include galvanic square waves, potential square waves, or a combination thereof.

The method, in some embodiments, can further include applying a coating including a polymer to the nano-structured surface.

In some embodiments, the endoprosthesis can be a bioerodible stent.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1A:
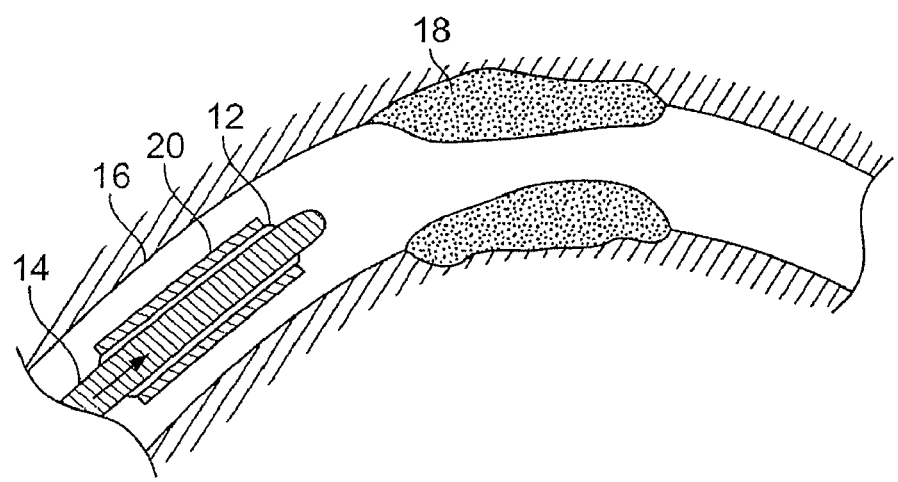
FIGS. 1A-1C are longitudinal cross-sectional views illustrating delivery of a stent in a collapsed state, expansion of the stent, and deployment of the stent.
Figure 1B:
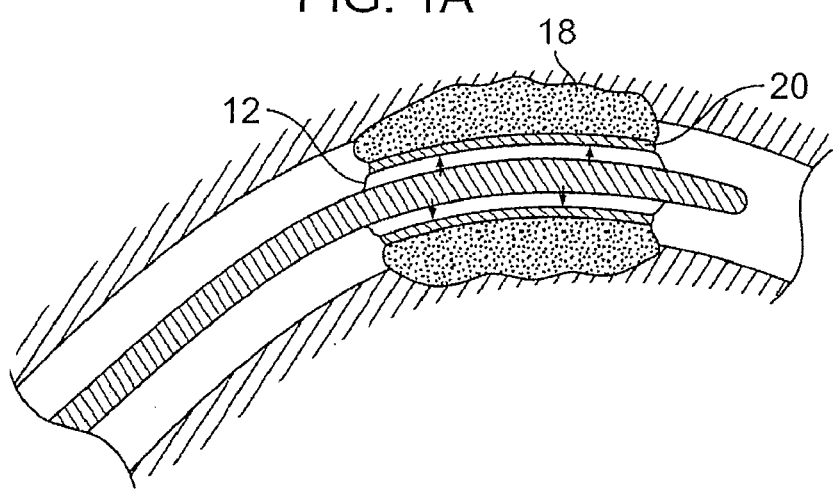
Figure 1C:
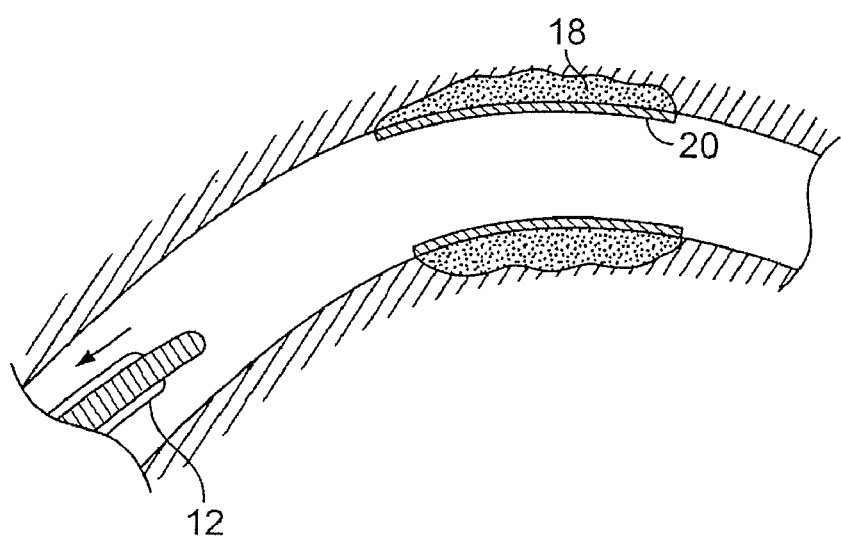

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
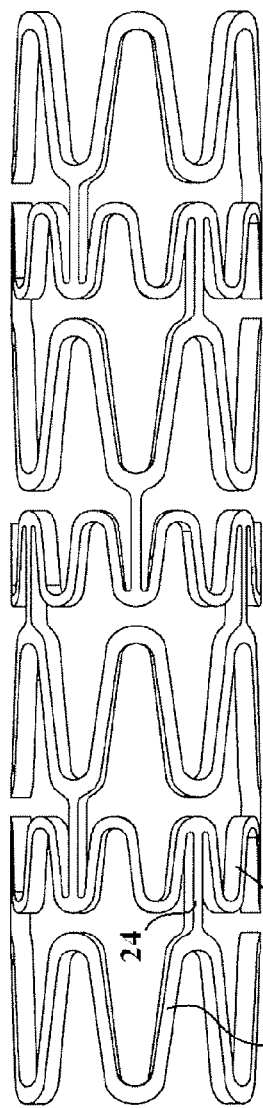
FIG. 2 is a perspective view of an embodiment of an expanded stent.

Referring to FIG. 2, a balloon-expandable stent 20 can have a stent body having the form of a tubular member defined by a plurality of bands 22 and a plurality of connectors 24 that extend between and connect adjacent bands. During use, bands 22 can be expanded from an initial, smaller diameter to a larger diameter to contact stent 20 against a wall of a vessel, thereby maintaining the patency of the vessel. Connectors 24 can provide stent 20 with flexibility and conformability that allow the stent to adapt to the contours of the vessel. The stent 20 defines a flow passage therethrough and is capable of maintaining patency in a blood vessel.

The stent 20 can include a body including iron or an alloy thereof. In some embodiments, the stent 20 can include a body including one or more bioerodible metals, such as magnesium, zinc, iron, or alloys thereof. The body can have a surface including iron oxide.

The stent body can have a surface having a morphology characterized by high-surface-area porous nano-structures. The nano-structured surface can provide a high surface area characterized by crevices between and around spaced individual nano-structures. For example, the individual nano-structures can be in the form of grains or flakes. The nano-structured surface can trigger and accelerate the rate of erosion or degradation of the bioerodible metal of the body of the stent. Additionally, select areas of a stent body can be treated to have the nano-structured surface to allow for select areas of stent degradation. Additionally, the nano-structured surface can allow for coatings to be deposited and interlock into the surface, enhancing adhesion. In some embodiments, the surface can also encourage endothelial growth to enhance endothelialization of the stent 20. The nano-structured surface may also allow for greater freedom of motion and a stent body that is less likely to fracture as the stent is flexed in use prior from the controlled bioerosion of the stent body. The stresses can be caused by flexure of the stent, during expansion or contraction of the stent or as the stent is delivered through a tortuously curved body lumen increase as a function of the distance from the stent axis. As a result, in some embodiments, the nano-structured surface can be on abluminal regions of the surface of the stent body or at other high stress points, such as the regions of the bands 22 adjacent to the connectors 24 which undergo greater flexure during expansion or contraction.

The nano-structured surface can be characterized by its visual appearance, the size and arrangement of individual nano-structures, its roughness and/or its resistance to corrosion. Examples of surfaces having the morphological features are shown in FIGS. 3A-3F. In some embodiments, the morphology of the surface can include "corn flake" and/or "rice grain" microstructures.

Figure 3A:
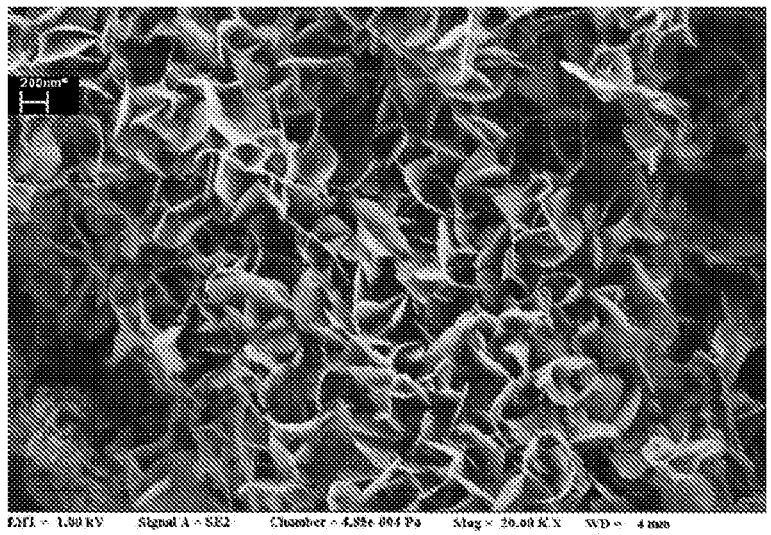
FIGS. 3A-3F depict examples of a surface having nano-structures having height to thickness aspect ratios of at least 5:1.
Figure 3B:
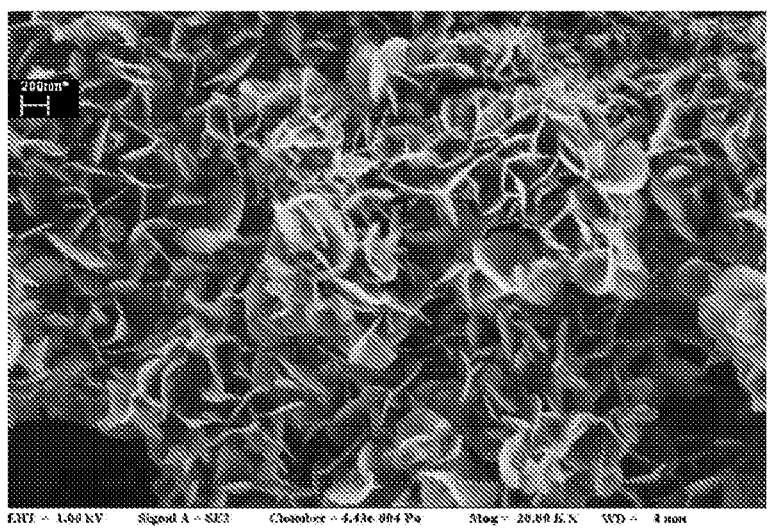
Figure 3C:
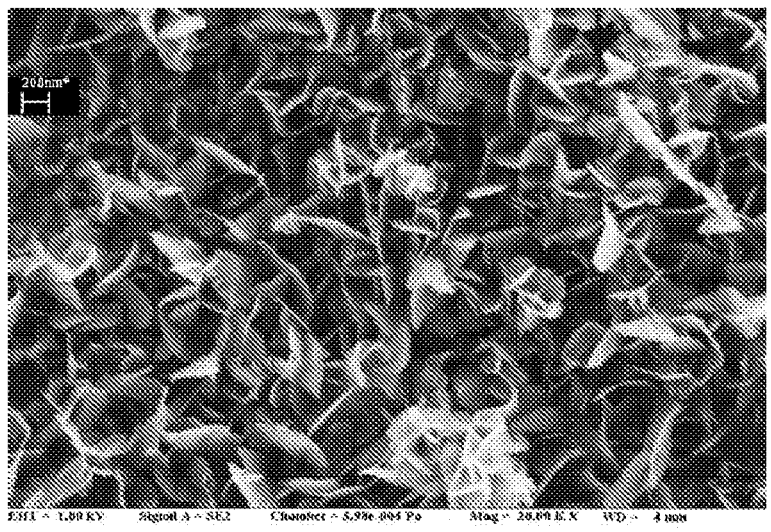

FIGS. 3A-3C depict a nano-structured surface characterized by definable thin planar flakes resembling corn flakes. The "corn flake" surface structures can have a height, H, of about 50 to 500 nm, e.g., about 100-300 nm, a width, W, of about 100 to 500 nm, e.g., about 200-400 nm, and a thickness, T, of about 5 to 50 nm, e.g., about 10-15 nm. The "corn flake" structures can have an aspect ratio of the height to the thickness of about 5:1 or more, e.g., 10:1 to 20:1. The "corn flake" structures can overlap in one or more layers. The separation between adjacent "corn flake" structures can be about 1-50 nm.

Figure 3D:
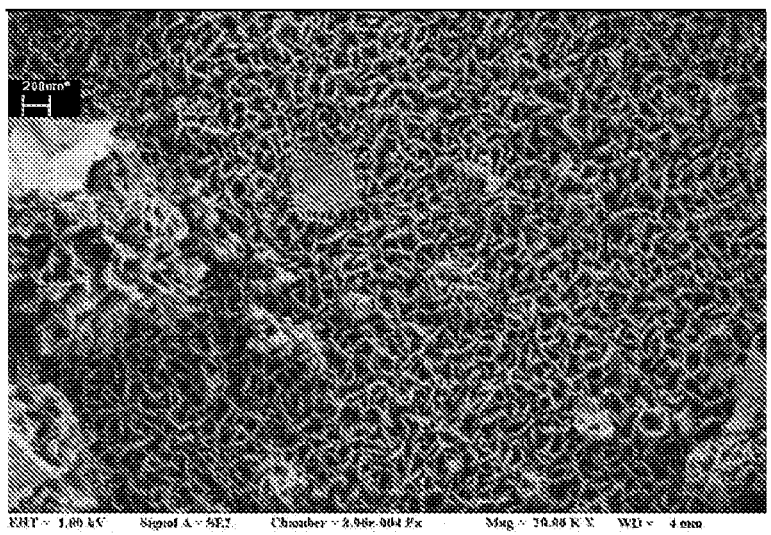
Figure 3E:
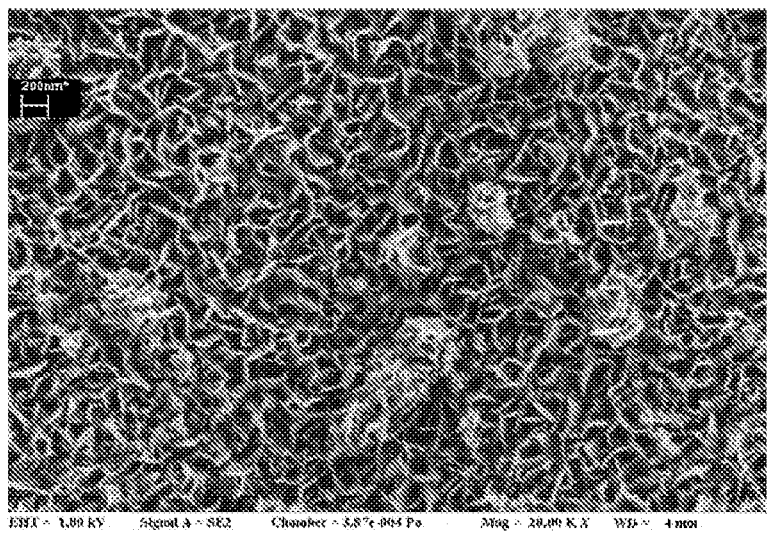
Figure 3F:
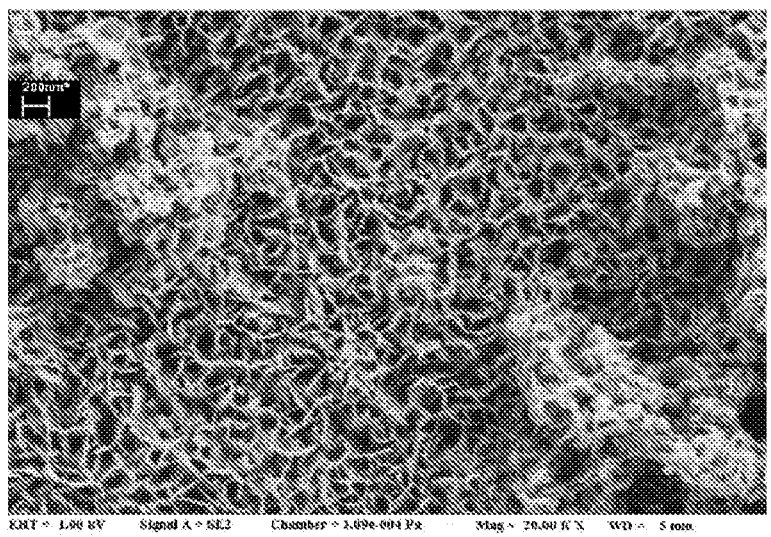

FIGS. 3D-3F depict a nano-structured surface characterized by definable sub-micron sized grains resembling rice grains. The "rice grains" surface structures can have a height, H, of about 50 to 500 nm, e.g. about 100-300 nm, and an average diameter, D, of about 5 nm to 50 nm, e.g. about 10-15 nm. The "rice grain" structures have an aspect ratio of the height to the diameter of about 5:1 or more, e.g. 10:1 to 20:1. The "rice grain" structures can overlap in one or more layers. The separation between adjacent "rice grain" structures can be about 1-50 nm.

The roughness of the nano-structured surface can also be characterized by the average roughness, $S_a$, the root mean square roughness, $S_q$, and/or the developed interfacial area ratio, $S_{dr}$. The $S_a$ and $S_q$ parameters represent an overall measure of the texture of the surface. $S_a$ and $S_q$ are relatively insensitive in differentiating peaks, valleys and the spacing of the various texture features. Surfaces with different visual morphologies can have similar $S_a$ and $S_q$ values. For a surface type, the $S_a$ and $S_q$ parameters indicate significant deviations in the texture characteristics. $S_{dr}$ is expressed as the percentage of additional surface area contributed by the texture as compared to an ideal plane the size of the measurement region. $S_{dr}$ further differentiates surfaces of similar amplitudes and average roughness. Typically $S_{dr}$ will increase with the spatial intricacy of the texture whether or not $S_a$ changes. In some embodiments, where the surface of the body has a nano-structured surface, the $S_{dr}$ can be about 100 or more, e.g. about 120 to 200. For example, the surface can have an $S_{dr}$ of about 150. In addition or in the alternative, the morphology can have an $S_q$ of about 20 or more, e.g. about 20 to 30.

The corrosion resistance of the high-surface-area porous nano-structures of iron, having iron oxide at the surface, can be less than 5 Kohms, e.g., about 2 Kohms. This represents a significantly reduced resistance to corrosion when compared to iron having a smooth surface finish, which has a corrosion resistance of about 20 Kohms. The resistance to corrosion can be calculated by Electrochemical Impedance Spectroscopy ("EIS") data. An example of how EIS data can be used to calculate the resistance to corrosion is described in *Analysis and Interpretation of EIS Data for Metals and Alloys*, Technical Report No. 26, Florian Mansfeld (Solartron Limited, 1999).

In some embodiments, the morphology of the surface can exhibit high uniformity. In other embodiments, select portions of the stent can be differentially treated to result in a stent having regions of preferential erosion. Uniformity can provide predictable mechanical performance and a constant rate of erosion. In some embodiments, a uniform morphology of the surface of the body can allow for the uniform adhesion of a coating applied to the surface. The uniformity of the morphology as characterized by $S_a$, $S_q$ or $S_{dr}$ and/or average peak spacing parameters can be within about +/−20% or less, e.g. +/−10% or less within a 1 μm square. In a given stent region, the uniformity can be within about +/−10%, e.g. about +/−1%. For example, in some embodiments, the ceramic exhibits high uniformity over an entire surface region of stent, such as the entire abluminal or adluminal surface, or a portion of a surface region, such as the center 25% or 50% of the surface region. The uniformity is expressed as standard deviation. Uniformity in a region of a stent can be determined by determining the average in five randomly chosen 1 μm square regions and calculating the standard deviation. Uniformity of visual morphology type in a region is determined by inspection of FESEM data at 50 KX.

The above described high-surface-area porous nano-structures can be produced on an iron stent body by electrochemical treatments. These electrochemical treatments can result in the presence of iron oxide on the surface of the resulting nano-structures. These electrochemical treatments can include anodic dissolution while cycling between positive and negative potential pulses. The cycling of potential pulses can be by galvanic square waves ("GSW") or by potential square waves ("PSW"). For example, an iron stent body precursor can be modified to have the above described high-surface area porous nano-structures by exposing the precursor iron stent body, cleaned of surface impurities, to a 1 mol $dm^{-3}$ NaOH solution and applying potential pulses cycling voltammetry at a sweep rate of 50 mV $s^{-1}$ between −1.2 V and 0.5 V, or by square-wave (SQW) potential pulses between −1.2 V and 0.5 V at 0.017 Hz, for 1 hour at a temperature of 200° C. In some embodiments, particular portions of an iron stent body can be modified to have the above described nano-structure by selectively exposing different portions of the iron stent body precursor to an electrolyte, such as sodium hydroxide. For example, droplets of NaOH can be applied to select regions of the stent body precursor to create corrosion enhancing regions 26 of selected struts of the stent 20.

Figure 4A:
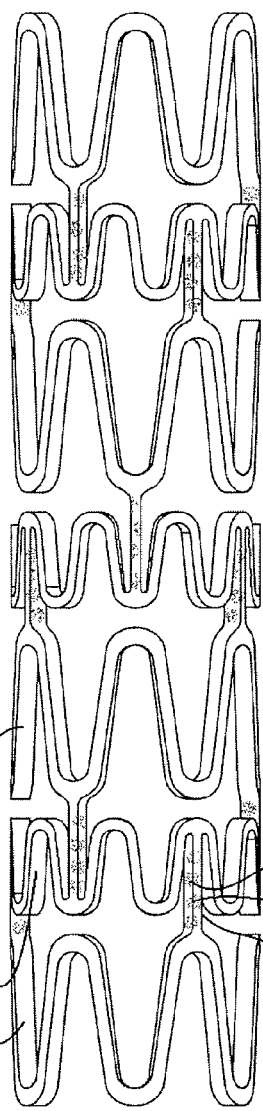
FIG. 4A depicts a stent having corrosion enhancing regions on connectors between bands.
Figure 4B:
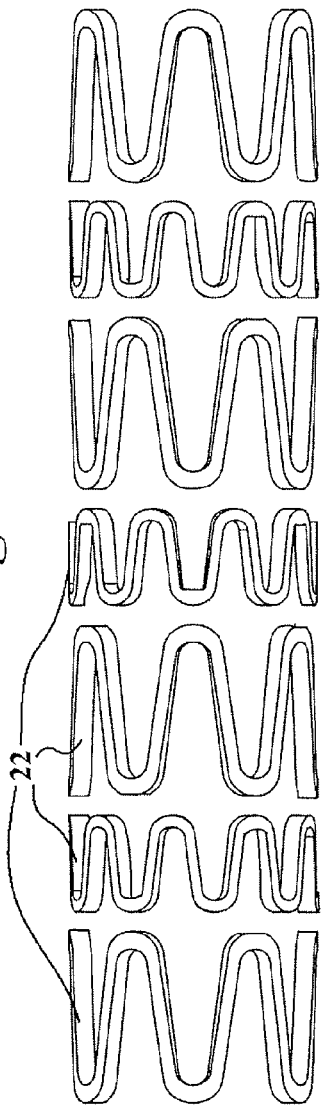
FIG. 4B depicts a stent after the erosion of the connectors between bands.

The stent body, in some embodiments, can have a surface with select regions having the high-surface-area surface morphologies so that the stent can degrade in a controlled manner. For example, as shown in FIG. 4A, the connectors 24 of the stent 20 can include corrosion enhancing regions 26. Such an arrangement can allow for the connectors 24 to degrade first, which can increase the flexibility of the stent along the longitudinal axis while radial opposition to the vessel wall is maintained. FIG. 4B depicts the stent after the erosion of the connectors 24, leaving the unconnected bands 22 that can still provide radial vessel opposition.

Figure 5A:
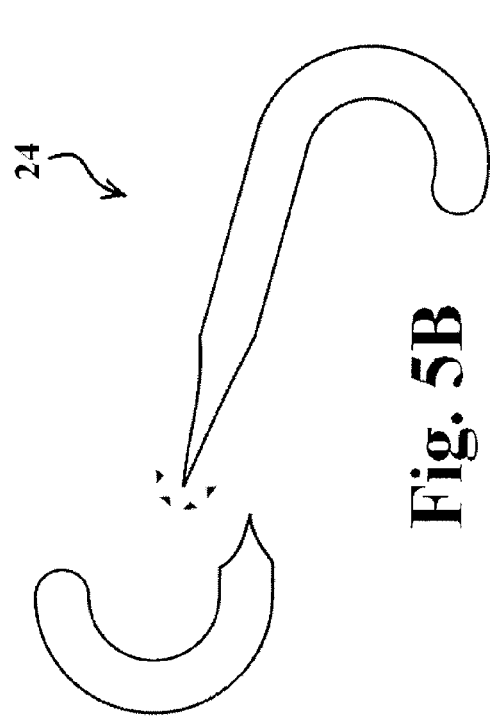
FIGS. 5A-5D depict how a stent strut erodes with and without spaced corrosion enhancing regions.
Figure 5B:
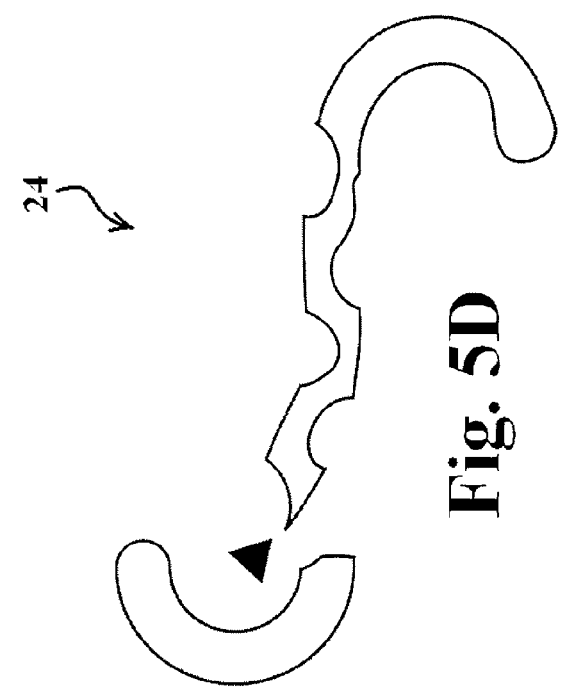
Figure 5C:
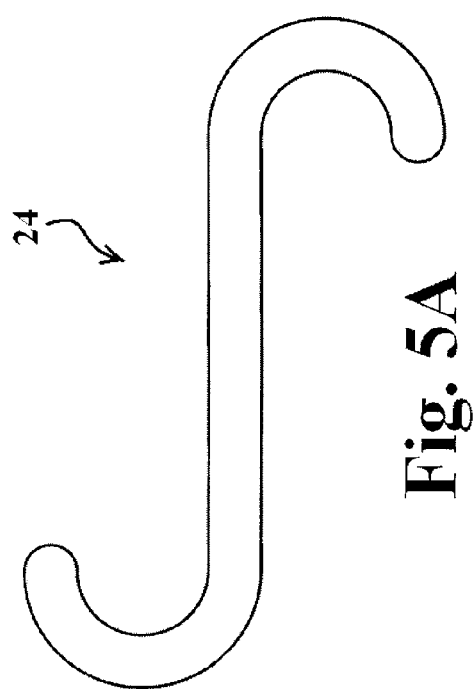
Figure 5D:
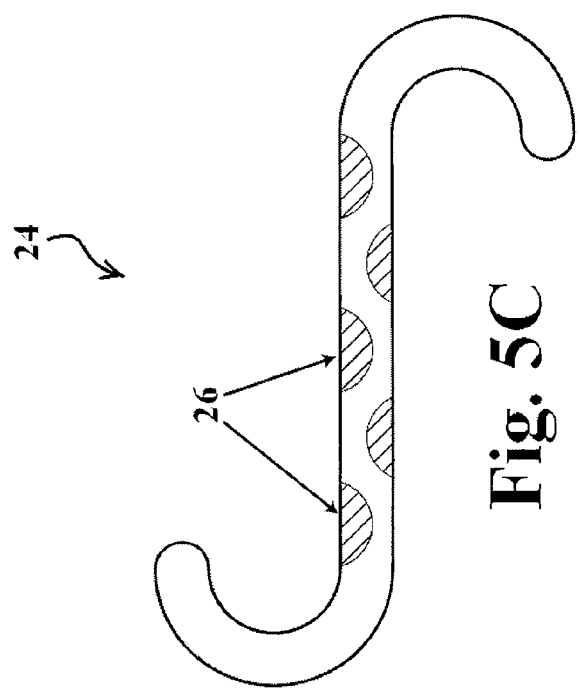

FIGS. 5A-5D show the difference between the uncontrolled erosion of a stent strut (e.g., portions of a band or a connector) and the erosion of a stent strut having corrosion enhancing regions 26. As shown by FIGS. 5A and 5B, uncontrolled degradation can cause struts to narrow and break in localized areas producing a sharp strut that retains its columnar strength, which can produce a piercing risk. A stent strut having spaced corrosion enhancing regions 26, however, can reduce the piercing risk. As shown in FIGS. 5C and 5D, corrosion enhancing regions 26 can erode to produce a strut having low columnar strength. Because the corrosion enhancing regions 26 can erode to produce an easily bent strut, the erosion of the stent strut produces a lower piercing risk. As discussed above, these corrosion enhancing regions 26 can be produced on an iron stent body precursor by applying droplets of an electrolyte (e.g., NaOH) to selected portions of the stent struts and then applying potential pulses cycling voltammetry between positive and negative pulses.

The stent body can, in some embodiments, include one or more coatings. In some embodiments, a block copolymer based on poly glutamic acid (PGA) can overlie the surface of the stent body. The block copolymer can, for example, be a di- or tri-block copolymer. Other blocks can be blocks of other biodegradable polymers such as poly(ethylene oxide) ("PEO"), polycaprolactam, poly(lactic-co-glycolic acid) ("PLGA"), or polysaccharides. In some embodiments, a block copolymer of PGA and a non-ionic polysaccharide, such as Pullulan, can overly the surface of the stent.

A block copolymer based on PGA can provide a robust interface adhesion with iron oxide present at the surface of the stent. In some embodiments a polyglutamic acid-pullulan coating can be applied to a iron stent having a surface including iron oxide to produce a stent having a strong bond between the stent body and the applied coating. Furthermore, in some embodiments, the surface of the stent body can have the above described high-surface-area porous nano-structure morphology, which can also increase the adhesion of the block copolymer to the surface of the stent body.

The coating of the block copolymer based on PGA can be a drug eluding coating designed to deliver a therapeutic agent to the surrounding tissue as the coating and the stent body erodes. The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule it is meant an organic molecule having 50 or fewer carbon atoms, and fewer than 100 non-hydrogen atoms in total.

Exemplary non-genetic therapeutic agents for use in conjunction with the presently disclosed endoprostheses an include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick anti-platelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine); (u) bARKct inhibitors; (v) phospholamban inhibitors; (w) Serca 2 gene/protein; (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well as derivatives of the forgoing, among others.

Exemplary genetic therapeutic agents for use in conjunction with the presently disclosed endoprostheses include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor; (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the presently disclosed endoprostheses include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the presently disclosed endoprostheses and include one or more of the following: (a) Ca-channel blockers including benzothiazapines such as diltiazem and clentiazem, dihydropyridines such as nifedipine, amlodipine and nicardapine, and phenylalkylamines such as verapamil; (b) serotonin pathway modulators including: 5-HT antagonists such as ketanserin and naftidrofuryl, as well as 5-HT uptake inhibitors such as fluoxetine; (c) cyclic nucleotide pathway agents including phosphodiesterase inhibitors such as cilostazole and dipyridamole, adenylate/Guanylate cyclase stimulants such as forskolin, as well as adenosine analogs; (d) catecholamine modulators including α-antagonists such as prazosin and bunazosine, β-antagonists such as propranolol and α/β-antagonists such as labetalol and carvedilol; (e) endothelin receptor antagonists; (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine; (g) ACE inhibitors such as cilazapril, fosinopril and enalapril; (h) ATII-receptor antagonists such as saralasin and losartin; (i) platelet adhesion inhibitors such as albumin and polyethylene oxide; (j) platelet aggregation inhibitors including cilostazole, aspirin and thienopyridine (ticlopidine, clopidogrel) and GP IIb/IIIa inhibitors such as abciximab, epitifibatide and tirofiban; (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C; (l) cyclooxygenase pathway inhibitors such as aspirin, ibuprofen, flurbiprofen, indomethacin and sulfinpyrazone; (m) natural and synthetic corticosteroids such as dexamethasone, prednisolone, methprednisolone and hydrocortisone; (n) lipoxygenase pathway inhibitors such as nordihydroguairetic acid and caffeic acid; (o) leukotriene receptor antagonists, (p) antagonists of E- and P-selectins; (q) inhibitors of VCAM-1 and ICAM-1 interactions; (r) prostaglandins and analogs thereof including prostaglandins such as PGE1 and PGI2 and prostacyclin analogs such as ciprostene, epoprostenol, carbacyclin, iloprost and beraprost; (s) macrophage activation preventers including bisphosphonates; (t) HMG-CoA reductase inhibitors such as lovastatin, pravastatin, fluvastatin, simvastatin and cerivastatin; (u) fish oils and omega-3-fatty acids; (v) free-radical scavengers/antioxidants such as probucol, vitamins C and E, ebselen, trans-retinoic acid and SOD mimics; (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives; (x) MMP pathway inhibitors such as marimastat, ilomastat and metastat; (y) cell motility inhibitors such as cytochalasin B; (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin, macrolide antibiotics such as erythromycin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin; (aa) matrix deposition/organization pathway inhibitors such as halofuginone or other quinazolinone derivatives and tranilast; (bb) endothelialization facilitators such as VEGF and RGD peptide, and (cc) blood rheology modulators such as pentoxifylline.

Further additional therapeutic agents include immunosuppressents such as sirolimus and antibiotics such as macrolide antibiotics, evorolimus, zotarolimus, tacrolimus, picrolimus, and Tacrolimus for the presently disclosed endoprostheses are also disclosed in U.S. Pat. No. 5,733,925.

Where a therapeutic agent is included, a wide range of therapeutic agent loadings can be used in conjunction with the presently disclosed block copolymer of PGA, with the therapeutically effective amount being readily determined by those of ordinary skill in the art and ultimately depending, for example, upon the condition to be treated, the age, sex and condition of the patient, the nature of the therapeutic agent, the erosion rate of the block copolymer of PGA and/or the stent body, and/or the nature of the stent itself, among other factors.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721). The ceramics can be used with other endoprostheses or medical devices, such as catheters, guide wires, and filters.

All publications, patent applications, patents, and other references mentioned herein including the appendix, are incorporated by reference herein in their entirety.

A number of embodiments have been described. Nevertheless, it will be understood that various modifications may be made without departing from the spirit and scope of this disclosure. Accordingly, other embodiments are within the scope of the following claims.

What is claimed is:

1. An endoprosthesis comprising a body defining a flow passage therethrough, the body capable of maintaining patency in a blood vessel, the body comprising iron or an alloy thereof, the body having a nano-structured surface comprising iron oxide in which the individual nano-structures have a height to thickness aspect ratio of at least 5:1, wherein the individual nano-structures have a height of about 100-300 nm.

2. The endoprosthesis of claim 1, wherein the height to thickness aspect ratio is between 10:1 and 20:1.

3. The endoprosthesis of claim 1, wherein the individual nano-structures have a rice grain structure having a diameter of between about 5 nm to 50 nm.

4. The endoprosthesis of claim 1, wherein an average separation distance between adjacent individual nano-structures is between about 1 nm and 50 nm.

5. The endoprosthesis of claim 1, wherein the surface has a Sdr of between 120 and 200.

6. The endoprosthesis of claim 1, wherein the surface has a resistance to corrosion of less than 5 Kohms.

7. The endoprosthesis of claim 1, further comprising a polymer coating over at least a portion of the nano-structured surface.

8. The endoprosthesis of claim 7, wherein the polymer coating comprises a co-block polymer of polyglutamic acid and a polymer selected from the group consisting of poly (ethylene oxide), polycaprolactam, poly(lactic-co-glycolic acid), polysaccharides, or combinations thereof.

9. The endoprosthesis of claim 8, wherein the polymer comprises a co-block polymer of polyglutamic acid and a non-ionic polysaccharide.

10. The endoprosthesis of claim 9, wherein the non-ionic polysaccharide is pullulan.

11. The endoprosthesis of claim 7, wherein the polymer coating is a drug eluting coating comprising a therapeutic agent.

12. The endoprosthesis of claim 1, wherein the endoprosthesis is bioerodible.

13. The endoprosthesis of claim 1, wherein the endoprosthesis is a stent.

14. The endoprosthesis of claim 1, wherein the individual nano-structures have a thickness of about 10-15 nm.

15. The endoprosthesis of claim 14, wherein the individual nano-structure have a rice grain structure having a diameter of about 10-15 nm.

16. The endoprosthesis of claim 14, wherein the individual nano-structures have a flake structure each having a width of about 200-400 nm.

17. An endoprosthesis comprising a body defining a flow passage therethrough, the body capable of maintaining patency in a blood vessel, the body comprising iron or an alloy thereof, the body having a nano-structured surface comprising iron oxide in which the individual nano-structures have a height to thickness aspect ratio of at least 5:1, wherein the individual nano-structures have a height of between about 50 nm to about 500 nm, wherein the individual nano-structures have a flake structure each having a width of at least twice the thickness, wherein the thickness of each individual nano-structure is between about 5 nm to 50 nm and the width of each individual nano-structure is between about 100 nm to 500 nm.

18. An endoprosthesis comprising a body defining a flow passage therethrough, the body capable of maintaining patency in a blood vessel, the body comprising iron or an alloy thereof, the body having a surface comprising iron oxide, the endoprosthesis comprising a coating over the surface, the coating comprising a co-block polymer of polyglutamic acid.

19. The endoprosthesis of claim 18, wherein the co-block polymer of polyglutamic acid is a co-block polymer of polyglutamic acid and of a polysaccharide.

20. The endoprosthesis of claim 19, wherein the polysaccharide is a non-ionic polysaccharide.

21. The endoprosthesis of claim 19, wherein the polysaccharide is pullulan.

22. The endoprosthesis of claim 18, wherein the surface has a Sdr between 120 and 200.

23. The endoprosthesis of claim 18, wherein the endoprosthesis is bioerodible.

24. The endoprosthesis of claim 18, wherein the endoprosthesis is a stent.

* * * * *